(12) United States Patent
Mason et al.

(10) Patent No.: US 10,080,799 B2
(45) Date of Patent: Sep. 25, 2018

(54) METHODS AND COMPOSITIONS RELATED TO GLYCOPROTEIN-IMMUNOGLOBULIN FUSIONS

(75) Inventors: Hugh S. Mason, Phoenix, AZ (US); Seong Hee Bhoo, Kyunggido (KR); Sun Hee Rosenthal, Santa Ana, CA (US); Charles J. Arntzen, Gold Canyon, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 1275 days.

(21) Appl. No.: 13/578,575

(22) PCT Filed: Feb. 11, 2011

(86) PCT No.: PCT/US2011/024466
§ 371 (c)(1),
(2), (4) Date: Oct. 29, 2012

(87) PCT Pub. No.: WO2011/100508
PCT Pub. Date: Aug. 18, 2011

(65) Prior Publication Data
US 2013/0045205 A1    Feb. 21, 2013

Related U.S. Application Data

(60) Provisional application No. 61/304,178, filed on Feb. 12, 2010.

(51) Int. Cl.
*A61K 39/29* (2006.01)
*C07K 19/00* (2006.01)
*C07K 16/10* (2006.01)
*A61K 39/12* (2006.01)
*A61K 38/00* (2006.01)
*A61K 39/00* (2006.01)

(52) U.S. Cl.
CPC ............. *A61K 39/29* (2013.01); *A61K 39/12* (2013.01); *C07K 16/10* (2013.01); *A61K 38/00* (2013.01); *A61K 2039/55566* (2013.01); *C07K 2317/13* (2013.01); *C07K 2317/24* (2013.01); *C07K 2319/30* (2013.01); *C12N 2760/14134* (2013.01); *C12N 2770/24234* (2013.01); *Y02A 50/397* (2018.01)

(58) Field of Classification Search
None
See application file for complete search history.

(56) References Cited

U.S. PATENT DOCUMENTS

| | | | |
|---|---|---|---|
| 3,791,932 A | 2/1974 | Schuurs et al. | 435/7.8 |
| 3,949,064 A | 4/1976 | Bornstein et al. | 436/527 |
| 4,174,384 A | 11/1979 | Ullman et al. | 436/537 |
| 4,554,101 A | 11/1985 | Hopp | 530/324 |
| 4,578,770 A | 3/1986 | Milani | 250/559.2 |
| 4,596,792 A | 6/1986 | Vyas | 424/185.1 |
| 4,599,230 A | 7/1986 | Milich et al. | 424/189.1 |
| 4,599,231 A | 7/1986 | Milich et al. | 424/189.1 |
| 4,601,903 A | 7/1986 | Frasch | 424/250.1 |
| 4,608,251 A | 8/1986 | Mia | 424/185.1 |
| 4,683,202 A | 7/1987 | Mullis | 435/91.2 |
| 4,684,611 A | 8/1987 | Schilperoort et al. | 435/468 |
| 4,879,236 A | 11/1989 | Smith et al. | 435/320.1 |
| 4,952,500 A | 8/1990 | Finnerty et al. | 435/69.1 |
| 5,084,269 A | 1/1992 | Kullenberg | 424/256.1 |
| 5,302,523 A | 4/1994 | Coffee et al. | 435/470 |
| 5,322,783 A | 6/1994 | Tomes et al. | 800/293 |
| 5,384,253 A | 1/1995 | Krzyzek et al. | 800/292 |
| 5,464,765 A | 11/1995 | Coffee et al. | 435/470 |
| 5,538,877 A | 7/1996 | Lundquist et al. | 800/265 |
| 5,538,880 A | 7/1996 | Lundquist et al. | 800/265 |
| 5,550,318 A | 8/1996 | Adams et al. | 800/300.1 |
| 5,563,055 A | 10/1996 | Townsend et al. | 800/294 |
| 5,580,859 A | 12/1996 | Felgner et al. | 514/44 R |
| 5,589,466 A | 12/1996 | Felgner et al. | 514/44 R |
| 5,591,616 A | 1/1997 | Hiei et al. | 435/469 |
| 5,610,042 A | 3/1997 | Chang et al. | 800/288 |
| 5,656,610 A | 8/1997 | Shuler et al. | 514/44 R |
| 5,702,932 A | 12/1997 | Hoy et al. | 800/25 |
| 5,736,524 A | 4/1998 | Content et al. | 514/44 R |
| 5,780,448 A | 7/1998 | Davis | 514/44 R |
| 5,789,215 A | 8/1998 | Berns et al. | 800/25 |
| 5,871,986 A | 2/1999 | Boyce | 435/183 |
| 5,925,565 A | 7/1999 | Berlioz et al. | 435/325 |
| 5,928,906 A | 7/1999 | Koster et al. | 435/91.2 |
| 5,935,819 A | 8/1999 | Eichner et al. | 435/96.4 |
| 5,945,100 A | 8/1999 | Fick | 424/93.21 |

(Continued)

FOREIGN PATENT DOCUMENTS

| WO | WO 94/09699 | 5/1994 |
|---|---|---|
| WO | WO 95/06128 | 3/1995 |

OTHER PUBLICATIONS

Allaway et al (AIDS Research and Human Retroviruses, 11(5), 1995).*
Choo et al (PNAS, 91, pp. 1294-1298, 1994).*
Cox et al (Exp. Hematol, 2004, 32(5): 441-449).*
GenBank Accession No. P06310 (published online 2005; see alignment in Non-Final office action).*
Canizares et al., *Immunol. Cell Biol.*, 83(3) :263-70, 2005.
Chargelegue et al., *Infect. Immun.* 73, 5915-5922, 2005.
Chen, *Biological Engineering*, 1(4) :291-321, 2008.
Floss et al., *Transgenic Res.*, 16(3) :315-332, 2007.

(Continued)

*Primary Examiner* — Stephen G Uyeno
(74) *Attorney, Agent, or Firm* — Norton Rose Fulbright US LLP

(57) ABSTRACT

Disclosed herein are compositions and methods for eliciting immune responses against HCV antigens. In particular embodiments, the compounds and methods elicit immune responses against all or a segment of HCV glycoprotein E1 and/or HCV glycoprotein E2.

16 Claims, 8 Drawing Sheets
Specification includes a Sequence Listing.

(56) References Cited

U.S. PATENT DOCUMENTS

| | | | |
|---|---|---|---|
| 5,981,274 A | 11/1999 | Tyrrell et al. | 435/320.1 |
| 5,994,624 A | 11/1999 | Trolinder et al. | 800/278 |
| 6,121,020 A * | 9/2000 | Selby | C07K 14/005 |
| | | | 424/189.1 |
| 6,150,134 A * | 11/2000 | Maertens | A61K 39/12 |
| | | | 424/228.1 |
| 6,323,322 B1 | 11/2001 | Filipula et al. | 530/387.3 |
| 6,551,820 B1 | 4/2003 | Mason et al. | 435/320.1 |
| 6,651,655 B1 | 11/2003 | Licalsi et al. | 128/203.15 |
| 6,656,462 B2 | 12/2003 | Dondero et al. | 424/85.2 |
| 6,733,754 B2 | 5/2004 | Roberts et al. | 424/184.1 |
| 6,793,923 B2 | 9/2004 | Brown et al. | 424/184.1 |
| 6,814,971 B2 | 11/2004 | Roberts et al. | 424/240.1 |
| 7,696,322 B2 * | 4/2010 | Bleck | C07K 16/00 |
| | | | 424/133.1 |
| 7,906,625 B2 * | 3/2011 | Shen | C07K 16/18 |
| | | | 435/252.3 |
| 9,233,173 B2 * | 1/2016 | Faulstich | A61K 47/48492 |
| 2002/0098191 A1 * | 7/2002 | Beaudry | A61K 47/48661 |
| | | | 424/160.1 |
| 2004/0001844 A1 | 1/2004 | Holgersson | 424/185.1 |
| 2006/0078932 A1 * | 4/2006 | Maertens | C07K 14/005 |
| | | | 435/5 |
| 2006/0088819 A1 * | 4/2006 | Houghton | C07K 14/005 |
| | | | 435/5 |
| 2006/0141581 A1 * | 6/2006 | Gillies | C07K 14/5418 |
| | | | 435/69.52 |
| 2008/0063657 A1 * | 3/2008 | Powell | A61K 38/162 |
| | | | 424/192.1 |
| 2008/0075733 A1 | 3/2008 | Mjalli et al. | 424/178.1 |

OTHER PUBLICATIONS

Giritch et al., *Proc. Natl. Acad. Sci. USA*, 103(40):14701-6, 2006.
Gleba et al., *Curr. Opin. Biotechnol.*, 18(2):134-41, 2007.
Huang and Mason, Plant Biotechnol., J., 2:241-249, 2004.
Huang et al., Biotechnol. Bioeng. 106:9-17, 2010.
Huang et al., Biotechnol. Bioeng., 103:706-714, 2009.
International Preliminary Report on Patentability issued in PCT Application No. PCT/US2011/024466, dated Aug. 23, 2012.
International Search Report and Written Opinion issued in PCT Application No. PCT/US2011/024466, dated Oct. 25, 2011.
Lico et al., *J. Cell Physiol.*, 216(2):366-77, 2008.
Lindenbach and Rice, Nature, 436:933-938, 2005.
Ma et al., Nature, (Genetics), 4:794-805, 2003.
Ma et al., Vaccine, 23(15):1814-8, 2005.
Marillonnet et al., *Proc. Natl. Acad. Sci. USA*, 101(18):6852-7, 2004.
Mor et al, Biotechnol. Bioeng., 81(4):430-37, 2003.
Phoolcharoen et al., Plant Biotechnol J. in press 2011.
Santi et al., *Methods*, 40(1):66-76, 2006.
Santi et al., Vaccine, 26(15):1846-1854, 2008.
Stoger et al., Methods Mol. Biol., 248:301-18, 2004.
Yusibov et al., Drugs, 7(4):203-17, 2006.

* cited by examiner

FIG. 9

SEQUENCE LISTING

```
<160> NUMBER OF SEQ ID NOS: 39

<210> SEQ ID NO 1
<211> LENGTH: 9401
<212> TYPE: DNA
<213> ORGANISM: Hepatitis C virus

<400> SEQUENCE: 1
gccagccccc tgatggggc gacactccac catgaatcac tccctgtga ggaactactg      60 tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gatcaaccg ctcaatgcct ggagatttgg gcgtgccccc      240
gcaagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaaaaaa aaacaaacgt aacaccaacc gtcgcccaca ggacgtcaag ttcccgggtg     420
gcggtcagat cgttggtgga gtttacttgt tgccgcgcag gggccctaga ttgggtgtgc     480
gcgcgacgag aaagacttcc gagcggtcgc aacctcgagg tagacgtcag cctatcccca     540
aggctcgtcg gcccgagggc aggacctggg ctcagcccgg gtacccttgg cccctctatg     600
gcaatgaggg ctgcgggtgg gcgggatggc tcctgtctcc ccgtggctct cggcctagct     660
ggggccccac agacccccgg cgtaggtcgc gcaatttggg taaggtcatc gatacccttta    720 cgtgcggctt cgccgaccte atgggtaca taccgctcgt cggcgcccct cttggaggcg     780
ctgccagggc cctggcgcat ggcgtccggg ttctggaaga cggcgtgaac tatgcaacag     840
ggaaccttcc tggttgctct ttctctatct tccttctggc cctgctctct tgcttgactg     900
tgcccgcttc ggcctaccaa gtgcgcaact ccacggggct ttaccacgtc accaatgatt     960
gccctaactc gagtattgtg tacgaggcgg ccgatgccat cctgcacact ccggggtgcg    1020
tcccttgcgt tcgtgagggc aacgcctcga ggtgttgggt ggcgatgacc cctacggtgg    1080
ccaccaggga tggcaaactc cccgcgacgc agcttcgacg tcacatcgat ctgcttgtcg    1140
ggagcgccac cctctgttcg gccctctacg tgggggacct atgcgggtct gtctttcttg    1200
tcggccaact gttcaccttc tctcccaggc gccactggac gacgcaaggt tgcaattgct    1260
ctatctatcc cggccatata acgggtcacc gcatggcatg ggatatgatg atgaactggt    1320
cccctacgac ggcgttggta atggctcagc tgctccggat cccacaagcc atcttggaca    1380
tgatcgctgg tgctcactgg ggagtcctgg cgggcatagc gtattctcc atggtgggga    1440 actgggcgaa ggtcctggta gtgctgctgc tatttgccgg cgtcgacgcg gaaacccacg    1500
tcaccggggg aagtgccggc cacactgtgt ctggatttgt tagcctcctc gcaccaggcg    1560
ccaagcagaa cgtccagctg atcaacacca acggcagttg gcacctcaat gcacggccc    1620 tgaactgcaa tgatagcctc aacaccggct ggttggcagg gcttttctat caccacaagt    1680
```

```
tcaactcttc aggctgtcct gagaggctag ccagctgccg accccttacc gattttgacc      1740
agggctgggg ccctatcagt tatgccaacg gaagcggccc cgaccagcgc ccctactgct      1800
ggcactaccc cccaaaacct tgcggtattg tgcccgcgaa gagtgtgtgt ggtccggtat      1860
attgcttcac tcccagcccc gtggtggtgg gaacgaccga caggtcgggc gcgcccacct      1920
acagctgggg tgaaaatgat acggacgtct tcgtccttaa caataccagg ccaccgctgg      1980
gcaattggtt cggttgtacc tggatgaact caactggatt caccaaagtg tgcggagcgc      2040
ctccttgtgt catcggaggg gcgggcaaca acaccctgca ctgccccact gattgcttcc      2100
gcaagcatcc ggacgccaca tactctcggt gcggctccgg tccctggatc acacccaggt      2160
gcctggtcga ctacccgtat aggctttggc attatccttg taccatcaac tacaccatat      2220
ttaaaatcag gatgtacgtg ggaggggtcg aacacaggct ggaagctgcc tgcaactgga      2280
cgcggggcga acgttgcgat ctggaagaca gggacaggtc cgagctcagc ccgttactgc      2340
tgaccactac acagtggcag gtcctcccgt gttccttcac aaccctacca gccttgtcca      2400
ccggcctcat ccacctccac cagaacattg tggacgtgca gtacttgtac ggggtggggt      2460
caagcatcgc gtcctgggcc attaagtggg agtacgtcgt tctcctgttc cttctgcttg      2520
cagacgcgcg cgtctgctcc tgcttgtgga tgatgctact catatcccaa gcggaggcgg      2580
ctttggagaa cctcgtaata cttaatgcag catccctggc cgggacgcac ggtcttgtat      2640
ccttcctcgt gttcttctgc tttgcatggt atttgaaggg taagtgggtg cccggagcgg      2700
tctacacctt ctacgggatg tggcctctcc tcctgctcct gttggcgttg ccccagcggg      2760
cgtacgcgct ggacacggag gtggccgcgt cgtgtggcgg tgttgttctc gtcgggttga      2820
tggcgctgac tctgtcacca tattacaagc gctatatcag ctggtgcttg tggtggcttc      2880
agtattttct gaccagagtg gaagcgcaac tgcacgtgtg gattcccccc ctcaacgtcc      2940 gagggggcg cgacgccgtc atcttactca tgtgtgctgt acacccgact ctggtatttg      3000
acatcaccaa attgctgctg gccgtcttcg gaccccttg gattcttcaa gccagtttgc      3060
ttaaagtacc ctactttgtg cgcgtccaag gccttctccg gttctgcgcg ttagcgcgga      3120
agatgatcgg aggccattac gtgcaaatgg tcatcattaa gttaggggcg cttactggca      3180
cctatgttta taaccatctc actcctcttc gggactgggc gcacaacggc ttgcgagatc      3240
tggccgtggc tgtagagcca gtcgtcttct cccaaatgga gaccaagctc atcacgtggg      3300
gggcagatac cgccgcgtgc ggtgacatca tcaacggctt gcctgtttcc gcccgcaggg      3360
gccgggagat actgctcggg ccagccgatg gaatggtctc caaggggtgg aggttgctgg      3420
cgcccatcac ggcgtacgcc cagcagacaa ggggcctcct agggtgcata atcaccagcc      3480
taactggccg ggacaaaaac caagtggagg gtgaggtcca gattgtgtca actgctgccc      3540
aaaccttcct ggcaacgtgc atcaatgggg tgtgctggac tgtctaccac ggggccggaa      3600
cgaggaccat cgcgtcaccc aagggtcctg tcatccagat gtataccaat gtagaccaag      3660
accttgtggg ctggcccgct ccgcaaggta gccgctcatt gacaccctgc acttgcggct      3720
cctcggacct ttacctggtc acgaggcacg ccgatgtcat tccgtgcgc cggcggggtg      3780 atagcagggg cagcctgctg tcgcccggc ccatttccta cttgaaaggc tcctcggggg      3840
gtccgctgtt gtgccccgcg gggcacgccg tgggcatatt tagggccgcg gtgtgcaccc      3900
gtggagtggc taaggcggtg gactttatcc ctgtggagaa cctagagaca accatgaggt      3960
ccccggtgtt cacggataac tcctctctcc acagtagtgcc ccagagcttc caggtggctc      4020
```

```
acctccatgc tcccacaggc agcggcaaaa gcaccaaggt cccggctgca tatgcagctc    4080
agggctataa ggtgctagta ctcaacccct ctgttgctgc aacactgggc tttggtgctt    4140
acatgtccaa ggctcatggg atcgatccta acatcaggac cggggtgaga acaattacca    4200
ctggcagccc catcacgtac tccacctacg gcaagttcct tgccgacggc gggtgctcgg    4260
ggggcgctta tgacataata atttgtgacg agtgccactc cacggatgcc acatccatct    4320
tgggcatcgg cactgtcctt gaccaagcag agactgcggg ggcgagactg gttgtgctcg    4380
ccaccgccac ccctccgggc tccgtcactg tgccccatcc aacatcgag gaggttgctc     4440
tgtccaccac cggagagatc ccttttacg gcaaggctat ccccctcgaa gtaatcaagg     4500
gggggagaca tctcatcttc tgtcattcaa agaagaagtg cgacgaactc gccgcaaagc    4560
tggtcgcatt gggcatcaat gccgtggcct actaccgcgg tcttgacgtg tccgtcatcc    4620
cgaccagcgg cgatgttgtc gtcgtggcaa ccgatgccct catgaccggc tataccggcg    4680
acttcgactc ggtgatagac tgcaatacgt gtgtcaccca gacagtcgat ttcagccttg    4740
accctacctt caccattgag acaatcacgc tcccccagga tgctgtctcc cgcactcaac    4800
gtcggggcag gactggcagg gggaagccag gcatctacag atttgtggca ccgggggagc    4860
gcccctccgg catgttcgac tcgtccgtcc tctgtgagtg ctatgacgca ggctgtgctt    4920
ggtatgagct cacgcccgcc gagactacag ttaggctacg agcgtacatg aacaccccgg    4980
ggcttcccgt gtgccaggac catcttgaat tttgggaggg cgtctttaca ggcctcactc    5040
atatagatgc ccactttcta tcccagacaa agcagagtgg ggagaacctt ccttacctgg    5100
tagcgtacca agccaccgtg tgcgctaggg ctcaagcccc tccccatcg tgggaccaga     5160
tgtggaagtg tttgattcgc ctcaagccca ccctccatgg gccaacaccc ctgctataca    5220
gactgggcgc tgttcagaat gaaatcaccc tgacgcaccc agtcaccaaa tacatcatga    5280
catgcatgtc ggccgacctg gaggtcgtca cgagcacctg ggtgctcgtt ggcggcgtcc    5340
tggctgcttt ggccgcgtat tgcctgtcaa caggctgcgt ggtcatagtg gcagggtcg     5400
tcttgtccgg gaagccggca atcatacctg acagggaagt cctctaccga gagttcgatg    5460
agatggaaga gtgctctcag cacttaccgt acatcgagca agggatgatg ctcgccgagc    5520
agttcaagca gaaggccctc ggcctcctgc agaccgcgtc ccgtcaggca gaggttatcg    5580
cccctgctgt ccagaccaac tggcaaaaac tcgagacctt ctgggcgaag catatgtgga    5640
acttcatcag tgggatacaa tacttggcgg gcttgtcaac gctgcctggt aaccccgcca    5700
ttgcttcatt gatggcttt acagctgctg tcaccagccc actaaccact agccaaaccc     5760
tcctcttcaa catattgggg gggtgggtgg ctgcccagct cgccgccccc ggtgccgcta    5820
ctgcctttgt gggcgctggc ttagctgcg ccgccatcgg cagtgttgga ctggggaagg     5880
tcctcataga catccttgca gggtatggcg cgggcgtggc gggagctctt gtggcattca    5940
agatcatgag cggtgaggtc ccctccacgg aggacctggt caatctactg cccgccatcc    6000
tctcgcccgg agccctcgta gtcggcgtgg tctgtgcagc aatactgcgc cggcacgttg    6060
gcccgggcga gggggcagtg cagtggatga accggctgat agccttcgcc tccgggggga    6120
accatgtttc ccccacgcac tacgtgccgg agagcgatgc agctgcccgc gtcactgcca    6180
tactcagcag cctcactgta acccagctcc tgaggcgact gcaccagtgg ataagctcgg    6240
agtgtaccac tccatgctcc ggttcctggc taagggacat ctgggactgg atatgcgagg    6300
tgttgagcga ctttaagacc tggctaaaag ctaagctcat gccacagctg cctgggatcc    6360
cctttgtgtc ctgccagcgc gggtataagg gggtctggcg agtggacggc atcatgcaca    6420
```

```
ctcgctgcca ctgtggagct gagatcactg gacatgtcaa aaacgggacg atgaggatcg    6480
tcggtcctag gacctgcagg aacatgtgga gtgggacctt ccccattaat gcctacacca    6540
cgggccnctg tacccccctt cctgcgccga actacacgtt cgcgctatgg agggtgtctg    6600
cagaggaata tgtggagata aggcaggtgg gggacttcca ctacgtgacg ggtatgacta    6660
ctgacaatct caaatgcccg tgccaggtcc catcgcccga attttcaca gaattggacg     6720
gggtgcgcct acataggttt gcgcccccct gcaagccctt gctgcgggag gaggtatcat    6780
tcagagtagg actccacgaa tacccggtag ggtcgcaatt accttgcgag cccgaaccgg    6840
acgtggccgt gttgacgtcc atgctcactg atccctccca taacagca gaggcggccg      6900
ggcgaaggtt ggcgagggga tcaccccct ctgtggccag ctcctcggct agccagctat     6960
ccgctccatc tctcaaggca acttgcaccg ctaaccatga ctccctgat gctgagctca     7020
tagaggccaa cctcctatgg aggcaggaga tgggcggcaa catcaccagg gttgagtcag    7080
aaaacaaagt ggtgattctg gactccttcg atccgcttgt ggcggaggag gacgagcggg    7140
agatctccgt acccgcagaa atcctgcgga agtctcggag attcgcccag gccctgcccg    7200
tttgggcgcg gccggactat aaccccccgc tagtggagac gtggaaaaag cccgactacg    7260
aaccacctgt ggtccatggc tgtccgcttc cacctccaaa gtccctcct gtgcctccgc     7320
ctcggaagaa gcgacggtg gtcctcactg aatcaaccct atctactgcc ttggccgagc     7380
tcgccaccag aagctttggc agctcctcaa cttccggcat tacgggcgac aatacgacaa    7440
catcctctga gcccgcccct ctggctgcc ccccgactc cgacgctgag tcctattcct      7500
ccatgccccc cctggagggg gagcctgggg atccggatct tagcgacggg tcatggtcaa    7560
cggtcagtag tgaggccaac gcggaggatg tcgtgtgctg ctcaatgtct tactcttgga    7620
caggcgcact cgtcaccccg tgcgccgcgg aagaacagaa actgcccatc aatgcactaa    7680
gcaactcgtt gctacgtcac cacaattgg tgtattccac cacctcacgc agtgcttgcc     7740
aaaggcagaa gaaagtcaca tttgacagac tgcaagttct ggacagccat taccaggacg    7800
tactcaagga ggttaaagca gcggcgtcaa agtgaaggc taacttgcta tccgtagagg     7860
aagcttgcag cctgacgccc ccacactcag ccaaatccaa gtttggttat ggggcaaaag    7920
acgtccgttg ccatgccaga aaggccgtaa cccacatcaa ctccgtgtgg aaagaccttc    7980
tggaagacaa tgtaacacca atagacacta ccatcatggc taagaacgag gttttctgcg    8040
ttcagcctga aaggggggt cgtaagccag ctcgtctcat cgtgttcccc gatctgggcg     8100
tgcgcgtgtg cgaaaagatg gctttgtacg acgtggttac aaagctcccc ttggccgtga    8160
tgggaagctc ctacggattc caatactcac caggacagcg ggttgaattc ctcgtgcaag    8220
cgtgaagtc caagaaaacc ccaatggggt tctcgtatga tacccgctgc tttgactcca    8280
cagtcactga gagcgacatc cgtacggagg aggcaatcta ccaatgttgt gacctcgacc    8340
cccaagcccg cgtggccatc aagtccctca ccgagaggct ttatgttggg ggccctctta   8400
ccaattcaag gggggagaac tgcggctatc gcaggtgccg cgcgagcggc gtactgacaa    8460
ctagctgtgg taacaccctc acttgctaca tcaaggcccg ggcagcctgt cgagccgcag    8520
ggctccagga ctgcaccatg ctcgtgtgtg gcgacgactt agtcgttatc tgtgaaagcg    8580
cgggggtcca ggaggacgcg gcgagcctga gagccttcac ggaggctatg accaggtact   8640
ccgccccccc tgggaccccc ccacaaccag aatacgactt ggagctcata acatcatgct    8700
cctccaacgt gtcagtcgcc cacgacggcg ctggaaagag ggtctactac ctcacccgtg    8760
```

-continued

| | |
|---|---|
| accctacaac cccctcgcg agagctgcgt gggagacagc aagacacact ccagtcaatt | 8820 |
| cctggctagg caacataatc atgtttgccc ccacactgtg ggcgaggatg atactgatga | 8880 |
| cccatttctt tagcgtcctt atagccaggg accagcttga acaggccctc gattgcgaga | 8940 |
| tctacggggc ctgctactcc atagaaccac ttgatctacc tccaatcatt caaagactcc | 9000 |
| atggcctcag cgcattttca ctccacagtt actctccagg tgaaattaat agggtggccg | 9060 |
| catgcctcag aaaacttggg gtaccgccct tgcgagcttg gagacaccgg gcccggagcg | 9120 |
| tccgcgctag gcttctggcc agaggaggca gggctgccat atgtggcaag tacctcttca | 9180 |
| actgggcagt aagaacaaag ctcaaactca ctccaatagc ggccgctggc cagctggact | 9240 |
| tgtccggctg gttcacggct ggctacagcg ggggagacat ttatcacagc gtgtctcatg | 9300 |
| cccggccccg ctggatctgg ttttgcctac tcctgcttgc tgcagggta ggcatctacc | 9360 |
| tcctccccaa ccgatgaagg ttggggtaaa cactccggcc t | 9401 |

<210> SEQ ID NO 2
<211> LENGTH: 3011
<212> TYPE: PRT
<213> ORGANISM: Hepatitis C virus

<400> SEQUENCE: 2

```
Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
```

```
            260                 265                 270
Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Gly Cys
            290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Met Ala Gln
                    325                 330                 335

Leu Leu Arg Ile Pro Gln Ala Ile Leu Asp Met Ile Ala Gly Ala His
                    340                 345                 350

Trp Gly Val Leu Ala Gly Ile Ala Tyr Phe Ser Met Val Gly Asn Trp
                    355                 360                 365

Ala Lys Val Leu Val Val Leu Leu Phe Ala Gly Val Asp Ala Glu
            370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                    405                 410                 415

Asn Gly Ser Trp His Leu Asn Ser Thr Ala Leu Asn Cys Asn Asp Ser
                    420                 425                 430

Leu Asn Thr Gly Trp Leu Ala Gly Leu Phe Tyr His His Lys Phe Asn
                    435                 440                 445

Ser Ser Gly Cys Pro Glu Arg Leu Ala Ser Cys Arg Pro Leu Thr Asp
            450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Lys Pro Cys Gly Ile
                    485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
            515                 520                 525

Trp Gly Glu Asn Asp Thr Asp Val Phe Val Leu Asn Asn Thr Arg Pro
            530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
                    565                 570                 575

Asn Thr Leu His Cys Pro Thr Asp Cys Phe Arg Lys His Pro Asp Ala
                    580                 585                 590

Thr Tyr Ser Arg Cys Gly Ser Gly Pro Trp Ile Thr Pro Arg Cys Leu
            595                 600                 605

Val Asp Tyr Pro Tyr Arg Leu Trp His Tyr Pro Cys Thr Ile Asn Tyr
            610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                    645                 650                 655

Arg Asp Arg Ser Glu Leu Ser Pro Leu Leu Leu Thr Thr Thr Gln Trp
                    660                 665                 670

Gln Val Leu Pro Cys Ser Phe Thr Thr Leu Pro Ala Leu Ser Thr Gly
            675                 680                 685
```

-continued

Leu Ile His Leu His Gln Asn Ile Val Asp Val Gln Tyr Leu Tyr Gly
    690             695                 700

Val Gly Ser Ser Ile Ala Ser Trp Ala Ile Lys Trp Glu Tyr Val Val
705                 710                 715                 720

Leu Leu Phe Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Lys Trp Val Pro
770                 775                 780

Gly Ala Val Tyr Thr Phe Tyr Gly Met Trp Pro Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
        835                 840                 845

Phe Leu Thr Arg Val Glu Ala Gln Leu His Val Trp Ile Pro Pro Leu
850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
        915                 920                 925

Ile Gly Gly His Tyr Val Gln Met Val Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
        995                 1000                1005

Glu Ile Leu Leu Gly Pro Ala Asp Gly Met Val Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Cys Ile Ile Thr Ser Leu Thr Gly Arg Asp Lys Asn
    1040                1045                1050

Gln Val Glu Gly Glu Val Gln Ile Val Ser Thr Ala Ala Gln Thr
    1055                1060                1065

Phe Leu Ala Thr Cys Ile Asn Gly Val Cys Trp Thr Val Tyr His
    1070                1075                1080

Gly Ala Gly Thr Arg Thr Ile Ala Ser Pro Lys Gly Pro Val Ile
    1085                1090                1095

-continued

```
Gln Met Tyr Thr Asn Val Asp Gln Asp Leu Val Gly Trp Pro Ala
1100                1105                1110

Pro Gln Gly Ser Arg Ser Leu Thr Pro Cys Thr Cys Gly Ser Ser
1115                1120                1125

Asp Leu Tyr Leu Val Thr Arg His Ala Asp Val Ile Pro Val Arg
1130                1135                1140

Arg Arg Gly Asp Ser Arg Gly Ser Leu Leu Ser Pro Arg Pro Ile
1145                1150                1155

Ser Tyr Leu Lys Gly Ser Ser Gly Gly Pro Leu Leu Cys Pro Ala
1160                1165                1170

Gly His Ala Val Gly Ile Phe Arg Ala Ala Val Cys Thr Arg Gly
1175                1180                1185

Val Ala Lys Ala Val Asp Phe Ile Pro Val Glu Asn Leu Glu Thr
1190                1195                1200

Thr Met Arg Ser Pro Val Phe Thr Asp Asn Ser Ser Pro Pro Val
1205                1210                1215

Val Pro Gln Ser Phe Gln Val Ala His Leu His Ala Pro Thr Gly
1220                1225                1230

Ser Gly Lys Ser Thr Lys Val Pro Ala Ala Tyr Ala Ala Gln Gly
1235                1240                1245

Tyr Lys Val Leu Val Leu Asn Pro Ser Val Ala Ala Thr Leu Gly
1250                1255                1260

Phe Gly Ala Tyr Met Ser Lys Ala His Gly Ile Asp Pro Asn Ile
1265                1270                1275

Arg Thr Gly Val Arg Thr Ile Thr Thr Gly Ser Pro Ile Thr Tyr
1280                1285                1290

Ser Thr Tyr Gly Lys Phe Leu Ala Asp Gly Gly Cys Ser Gly Gly
1295                1300                1305

Ala Tyr Asp Ile Ile Ile Cys Asp Glu Cys His Ser Thr Asp Ala
1310                1315                1320

Thr Ser Ile Leu Gly Ile Gly Thr Val Leu Asp Gln Ala Glu Thr
1325                1330                1335

Ala Gly Ala Arg Leu Val Val Leu Ala Thr Ala Thr Pro Pro Gly
1340                1345                1350

Ser Val Thr Val Pro His Pro Asn Ile Glu Glu Val Ala Leu Ser
1355                1360                1365

Thr Thr Gly Glu Ile Pro Phe Tyr Gly Lys Ala Ile Pro Leu Glu
1370                1375                1380

Val Ile Lys Gly Gly Arg His Leu Ile Phe Cys His Ser Lys Lys
1385                1390                1395

Lys Cys Asp Glu Leu Ala Ala Lys Leu Val Ala Leu Gly Ile Asn
1400                1405                1410

Ala Val Ala Tyr Tyr Arg Gly Leu Asp Val Ser Val Ile Pro Thr
1415                1420                1425

Ser Gly Asp Val Val Val Ala Thr Asp Ala Leu Met Thr Gly
1430                1435                1440

Tyr Thr Gly Asp Phe Asp Ser Val Ile Asp Cys Asn Thr Cys Val
1445                1450                1455

Thr Gln Thr Val Asp Phe Ser Leu Asp Pro Thr Phe Thr Ile Glu
1460                1465                1470

Thr Ile Thr Leu Pro Gln Asp Ala Val Ser Arg Thr Gln Arg Arg
1475                1480                1485

Gly Arg Thr Gly Arg Gly Lys Pro Gly Ile Tyr Arg Phe Val Ala
```

```
                  1490              1495              1500

Pro Gly Glu Arg Pro Ser Gly Met Phe Asp Ser Ser Val Leu Cys
        1505              1510              1515

Glu Cys Tyr Asp Ala Gly Cys Ala Trp Tyr Glu Leu Thr Pro Ala
        1520              1525              1530

Glu Thr Thr Val Arg Leu Arg Ala Tyr Met Asn Thr Pro Gly Leu
        1535              1540              1545

Pro Val Cys Gln Asp His Leu Glu Phe Trp Glu Gly Val Phe Thr
        1550              1555              1560

Gly Leu Thr His Ile Asp Ala His Phe Leu Ser Gln Thr Lys Gln
        1565              1570              1575

Ser Gly Glu Asn Leu Pro Tyr Leu Val Ala Tyr Gln Ala Thr Val
        1580              1585              1590

Cys Ala Arg Ala Gln Ala Pro Pro Pro Ser Trp Asp Gln Met Trp
        1595              1600              1605

Lys Cys Leu Ile Arg Leu Lys Pro Thr Leu His Gly Pro Thr Pro
        1610              1615              1620

Leu Leu Tyr Arg Leu Gly Ala Val Gln Asn Glu Ile Thr Leu Thr
        1625              1630              1635

His Pro Val Thr Lys Tyr Ile Met Thr Cys Met Ser Ala Asp Leu
        1640              1645              1650

Glu Val Val Thr Ser Thr Trp Val Leu Val Gly Gly Val Leu Ala
        1655              1660              1665

Ala Leu Ala Ala Tyr Cys Leu Ser Thr Gly Cys Val Val Ile Val
        1670              1675              1680

Gly Arg Val Val Leu Ser Gly Lys Pro Ala Ile Ile Pro Asp Arg
        1685              1690              1695

Glu Val Leu Tyr Arg Glu Phe Asp Glu Met Glu Glu Cys Ser Gln
        1700              1705              1710

His Leu Pro Tyr Ile Glu Gln Gly Met Met Leu Ala Glu Gln Phe
        1715              1720              1725

Lys Gln Lys Ala Leu Gly Leu Leu Gln Thr Ala Ser Arg Gln Ala
        1730              1735              1740

Glu Val Ile Ala Pro Ala Val Gln Thr Asn Trp Gln Lys Leu Glu
        1745              1750              1755

Thr Phe Trp Ala Lys His Met Trp Asn Phe Ile Ser Gly Ile Gln
        1760              1765              1770

Tyr Leu Ala Gly Leu Ser Thr Leu Pro Gly Asn Pro Ala Ile Ala
        1775              1780              1785

Ser Leu Met Ala Phe Thr Ala Ala Val Thr Ser Pro Leu Thr Thr
        1790              1795              1800

Ser Gln Thr Leu Leu Phe Asn Ile Leu Gly Gly Trp Val Ala Ala
        1805              1810              1815

Gln Leu Ala Ala Pro Gly Ala Ala Thr Ala Phe Val Gly Ala Gly
        1820              1825              1830

Leu Ala Gly Ala Ala Ile Gly Ser Val Gly Leu Gly Lys Val Leu
        1835              1840              1845

Ile Asp Ile Leu Ala Gly Tyr Gly Ala Gly Val Ala Gly Ala Leu
        1850              1855              1860

Val Ala Phe Lys Ile Met Ser Gly Glu Val Pro Ser Thr Glu Asp
        1865              1870              1875

Leu Val Asn Leu Leu Pro Ala Ile Leu Ser Pro Gly Ala Leu Val
        1880              1885              1890
```

```
Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Ala Ile Leu Ser Ser Leu Thr Val
    1940                1945                1950

Thr Gln Leu Leu Arg Arg Leu His Gln Trp Ile Ser Ser Glu Cys
    1955                1960                1965

Thr Thr Pro Cys Ser Gly Ser Trp Leu Arg Asp Ile Trp Asp Trp
    1970                1975                1980

Ile Cys Glu Val Leu Ser Asp Phe Lys Thr Trp Leu Lys Ala Lys
    1985                1990                1995

Leu Met Pro Gln Leu Pro Gly Ile Pro Phe Val Ser Cys Gln Arg
    2000                2005                2010

Gly Tyr Lys Gly Val Trp Arg Val Asp Gly Ile Met His Thr Arg
    2015                2020                2025

Cys His Cys Gly Ala Glu Ile Thr Gly His Val Lys Asn Gly Thr
    2030                2035                2040

Met Arg Ile Val Gly Pro Arg Thr Cys Arg Asn Met Trp Ser Gly
    2045                2050                2055

Thr Phe Pro Ile Asn Ala Tyr Thr Thr Gly Pro Cys Thr Pro Leu
    2060                2065                2070

Pro Ala Pro Asn Tyr Thr Phe Ala Leu Trp Arg Val Ser Ala Glu
    2075                2080                2085

Glu Tyr Val Glu Ile Arg Gln Val Gly Asp Phe His Tyr Val Thr
    2090                2095                2100

Gly Met Thr Thr Asp Asn Leu Lys Cys Pro Cys Gln Val Pro Ser
    2105                2110                2115

Pro Glu Phe Phe Thr Glu Leu Asp Gly Val Arg Leu His Arg Phe
    2120                2125                2130

Ala Pro Pro Cys Lys Pro Leu Leu Arg Glu Glu Val Ser Phe Arg
    2135                2140                2145

Val Gly Leu His Glu Tyr Pro Val Gly Ser Gln Leu Pro Cys Glu
    2150                2155                2160

Pro Glu Pro Asp Val Ala Val Leu Thr Ser Met Leu Thr Asp Pro
    2165                2170                2175

Ser His Ile Thr Ala Glu Ala Ala Gly Arg Arg Leu Ala Arg Gly
    2180                2185                2190

Ser Pro Pro Ser Val Ala Ser Ser Ser Ala Ser Gln Leu Ser Ala
    2195                2200                2205

Pro Ser Leu Lys Ala Thr Cys Thr Ala Asn His Asp Ser Pro Asp
    2210                2215                2220

Ala Glu Leu Ile Glu Ala Asn Leu Leu Trp Arg Gln Glu Met Gly
    2225                2230                2235

Gly Asn Ile Thr Arg Val Glu Ser Glu Asn Lys Val Val Ile Leu
    2240                2245                2250

Asp Ser Phe Asp Pro Leu Val Ala Glu Glu Asp Glu Arg Glu Ile
    2255                2260                2265

Ser Val Pro Ala Glu Ile Leu Arg Lys Ser Arg Arg Phe Ala Gln
    2270                2275                2280
```

```
Ala Leu Pro Val Trp Ala Arg Pro Asp Tyr Asn Pro Pro Leu Val
2285                2290                2295

Glu Thr Trp Lys Lys Pro Asp Tyr Glu Pro Pro Val Val His Gly
2300                2305                2310

Cys Pro Leu Pro Pro Pro Lys Ser Pro Pro Val Pro Pro Pro Arg
2315                2320                2325

Lys Lys Arg Thr Val Val Leu Thr Glu Ser Thr Leu Ser Thr Ala
2330                2335                2340

Leu Ala Glu Leu Ala Thr Arg Ser Phe Gly Ser Ser Ser Thr Ser
2345                2350                2355

Gly Ile Thr Gly Asp Asn Thr Thr Thr Ser Ser Glu Pro Ala Pro
2360                2365                2370

Ser Gly Cys Pro Pro Asp Ser Asp Ala Glu Ser Tyr Ser Ser Met
2375                2380                2385

Pro Pro Leu Glu Gly Glu Pro Gly Asp Pro Asp Leu Ser Asp Gly
2390                2395                2400

Ser Trp Ser Thr Val Ser Ser Glu Ala Asn Ala Glu Asp Val Val
2405                2410                2415

Cys Cys Ser Met Ser Tyr Ser Trp Thr Gly Ala Leu Val Thr Pro
2420                2425                2430

Cys Ala Ala Glu Glu Gln Lys Leu Pro Ile Asn Ala Leu Ser Asn
2435                2440                2445

Ser Leu Leu Arg His His Asn Leu Val Tyr Ser Thr Thr Ser Arg
2450                2455                2460

Ser Ala Cys Gln Arg Gln Lys Lys Val Thr Phe Asp Arg Leu Gln
2465                2470                2475

Val Leu Asp Ser His Tyr Gln Asp Val Leu Lys Glu Val Lys Ala
2480                2485                2490

Ala Ala Ser Lys Val Lys Ala Asn Leu Leu Ser Val Glu Glu Ala
2495                2500                2505

Cys Ser Leu Thr Pro Pro His Ser Ala Lys Ser Lys Phe Gly Tyr
2510                2515                2520

Gly Ala Lys Asp Val Arg Cys His Ala Arg Lys Ala Val Thr His
2525                2530                2535

Ile Asn Ser Val Trp Lys Asp Leu Leu Glu Asp Asn Val Thr Pro
2540                2545                2550

Ile Asp Thr Thr Ile Met Ala Lys Asn Glu Val Phe Cys Val Gln
2555                2560                2565

Pro Glu Lys Gly Gly Arg Lys Pro Ala Arg Leu Ile Val Phe Pro
2570                2575                2580

Asp Leu Gly Val Arg Val Cys Glu Lys Met Ala Leu Tyr Asp Val
2585                2590                2595

Val Thr Lys Leu Pro Leu Ala Val Met Gly Ser Ser Tyr Gly Phe
2600                2605                2610

Gln Tyr Ser Pro Gly Gln Arg Val Glu Phe Leu Val Gln Ala Trp
2615                2620                2625

Lys Ser Lys Lys Thr Pro Met Gly Phe Ser Tyr Asp Thr Arg Cys
2630                2635                2640

Phe Asp Ser Thr Val Thr Glu Ser Asp Ile Arg Thr Glu Glu Ala
2645                2650                2655

Ile Tyr Gln Cys Cys Asp Leu Asp Pro Gln Ala Arg Val Ala Ile
2660                2665                2670

Lys Ser Leu Thr Glu Arg Leu Tyr Val Gly Gly Pro Leu Thr Asn
```

|  |  |  |  |  |  |  |  |  |  |
|---|---|---|---|---|---|---|---|---|---|
|  |  | 2675 |  |  | 2680 |  |  | 2685 |  |

Ser Arg Gly Glu Asn Cys Gly Tyr Arg Cys Arg Ala Ser Gly
    2690                2695                2700

Val Leu Thr Thr Ser Cys Gly Asn Thr Leu Thr Cys Tyr Ile Lys
    2705                2710                2715

Ala Arg Ala Ala Cys Arg Ala Ala Gly Leu Gln Asp Cys Thr Met
    2720                2725                2730

Leu Val Cys Gly Asp Leu Val Val Ile Cys Glu Ser Ala Gly
    2735                2740                2745

Val Gln Glu Asp Ala Ala Ser Leu Arg Ala Phe Thr Glu Ala Met
    2750                2755                2760

Thr Arg Tyr Ser Ala Pro Pro Gly Asp Pro Pro Gln Pro Glu Tyr
    2765                2770                2775

Asp Leu Glu Leu Ile Thr Ser Cys Ser Ser Asn Val Ser Val Ala
    2780                2785                2790

His Asp Gly Ala Gly Lys Arg Val Tyr Tyr Leu Thr Arg Asp Pro
    2795                2800                2805

Thr Thr Pro Leu Ala Arg Ala Ala Trp Glu Thr Ala Arg His Thr
    2810                2815                2820

Pro Val Asn Ser Trp Leu Gly Asn Ile Ile Met Phe Ala Pro Thr
    2825                2830                2835

Leu Trp Ala Arg Met Ile Leu Met Thr His Phe Phe Ser Val Leu
    2840                2845                2850

Ile Ala Arg Asp Gln Leu Glu Gln Ala Leu Asp Cys Glu Ile Tyr
    2855                2860                2865

Gly Ala Cys Tyr Ser Ile Glu Pro Leu Asp Leu Pro Pro Ile Ile
    2870                2875                2880

Gln Arg Leu His Gly Leu Ser Ala Phe Ser Leu His Ser Tyr Ser
    2885                2890                2895

Pro Gly Glu Ile Asn Arg Val Ala Ala Cys Leu Arg Lys Leu Gly
    2900                2905                2910

Val Pro Pro Leu Arg Ala Trp Arg His Arg Ala Arg Ser Val Arg
    2915                2920                2925

Ala Arg Leu Leu Ala Arg Gly Gly Arg Ala Ala Ile Cys Gly Lys
    2930                2935                2940

Tyr Leu Phe Asn Trp Ala Val Arg Thr Lys Leu Lys Leu Thr Pro
    2945                2950                2955

Ile Ala Ala Ala Gly Gln Leu Asp Leu Ser Gly Trp Phe Thr Ala
    2960                2965                2970

Gly Tyr Ser Gly Gly Asp Ile Tyr His Ser Val Ser His Ala Arg
    2975                2980                2985

Pro Arg Trp Ile Trp Phe Cys Leu Leu Leu Leu Ala Ala Gly Val
    2990                2995                3000

Gly Ile Tyr Leu Leu Pro Asn Arg
    3005                3010

<210> SEQ ID NO 3
<211> LENGTH: 501
<212> TYPE: DNA
<213> ORGANISM: Artificial Sequence
<220> FEATURE:
<223> OTHER INFORMATION: Synthetic primer

<400> SEQUENCE: 3
taccaagtga gaaactctac aggactttat catgttacta atgattgccc taattctagt    60

```
attgtttatg aggcagcaga tgcaattctt catactccag gatgtgttcc ttgtgttaga        120
gagggcaatg catcaagatg ctgggtagct atgacaccta ctgttgcaac cagggatggt        180
aaacttccag ctactcaact tagaagacat attgatttgc ttgtcggaag tgctactctc        240
tgtagtgctc tttacgtggg agacctctgc ggatctgtgt ttcttgtagg acaattgttt        300 acatttcac caaggagaca ttggactaca caaggttgca attgctctat ctatccagga         360
cacattacag gtcacagaat ggcatgggat atgatgatga attggtctcc tacaactgca        420
ttggtaatgg ctcagttgct cagaatccca caagctattt tggacatgat agctggtgct        480 cattgggag tccttgcagg c                                                   501
```

<210> SEQ ID NO 4
<211> LENGTH: 167
<212> TYPE: PRT
<213> ORGANISM: Artificial Sequence
<220> FEATURE:
<223> OTHER INFORMATION: Synthetic peptide

<400> SEQUENCE: 4

```
Tyr Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Met Thr Pro Thr Val Ala Thr Arg Asp Gly Lys Leu Pro Ala
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Gly
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Thr Ala Leu Val Met Ala
    130                 135                 140

Gln Leu Leu Arg Ile Pro Gln Ala Ile Leu Asp Met Ile Ala Gly Ala
145                 150                 155                 160

His Trp Gly Val Leu Ala Gly
                165
```

<210> SEQ ID NO 5
<211> LENGTH: 975
<212> TYPE: DNA
<213> ORGANISM: Artificial Sequence
<220> FEATURE:
<223> OTHER INFORMATION: Synthetic primer

<400> SEQUENCE: 5

```
gaaactcatg ttacaggtgg aagtgcagga cacactgtgt ctggatttgt tagtcttctt         60
gcaccaggag ccaaacaaaa tgtgcagctt attaacacta tggctcatg gcatctcaat        120 tcaactgcac tgaactgtaa tgattctctt aacacaggat ggttggcagg tctgttttat       180
catcacaagt tcaattcttc aggatgtcct gaaagattag cctcatgcag gcccacttact     240 gattttgatc aaggctgggg tcctattagt tatgcaaacg gatctggacc cgaccagaga       300
```

```
ccatattgtt ggcactaccc accaaaacct tgcggtattg ttcccgctaa gtcagtatgt      360
ggtcctgttt attgtttcac tccatcaccc gtggtagttg aacaacaga taggagtggc      420 gctccaacat attcctgggg tgaaaatgat actgatgtat ttgtgcttaa caacactagg     480
ccacctttgg gaaattggtt cggttgtact tggatgaact caactggatt caccaaagtc    540
tgtggtgctc ctccttgtgt tatcggaggg gctggaaaca acaccttgca ttgccccact    600
gattgtttta gaaacatcc tgatgccaca tactctaggt gcggctctgg tccttggatt      660
acaccaaggt gccttgtcga ctacccttat aggctttggc attatccttg tactattaac    720
tataccatct ttaaaattag aatgtatgtg ggaggtgtag agcacaggtt ggaagctgca    780
tgcaattgga caagaggtga aggtgcgat ttggaagata gggacaggtc agagctttca     840
cctttattgt tgacaactac acagtggcaa gtgctccctt gttccttcac aaccttacca    900
gccttgtcta ctggacttat ccacctccat cagaacattg ttgatgtgca gtatttgtac   960
ggtgtgggat caagt                                                     975
```

<210> SEQ ID NO 6
<211> LENGTH: 325
<212> TYPE: PRT
<213> ORGANISM: Artificial Sequence
<220> FEATURE:
<223> OTHER INFORMATION: Synthetic peptide

<400> SEQUENCE: 6

```
Glu Thr His Val Thr Gly Gly Ser Ala Gly His Thr Val Ser Gly Phe
1               5                   10                  15

Val Ser Leu Leu Ala Pro Gly Ala Lys Gln Asn Val Gln Leu Ile Asn
            20                  25                  30

Thr Asn Gly Ser Trp His Leu Asn Ser Thr Ala Leu Asn Cys Asn Asp
        35                  40                  45

Ser Leu Asn Thr Gly Trp Leu Ala Gly Leu Phe Tyr His His Lys Phe
    50                  55                  60

Asn Ser Ser Gly Cys Pro Glu Arg Leu Ala Ser Cys Arg Pro Leu Thr
65                  70                  75                  80

Asp Phe Asp Gln Gly Trp Gly Pro Ile Ser Tyr Ala Asn Gly Ser Gly
                85                  90                  95

Pro Asp Gln Arg Pro Tyr Cys Trp His Tyr Pro Pro Lys Pro Cys Gly
            100                 105                 110

Ile Val Pro Ala Lys Ser Val Cys Gly Pro Val Tyr Cys Phe Thr Pro
        115                 120                 125

Ser Pro Val Val Gly Thr Thr Asp Arg Ser Gly Ala Pro Thr Tyr
    130                 135                 140

Ser Trp Gly Glu Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Ala Gly
            180                 185                 190

Asn Asn Thr Leu His Cys Pro Thr Asp Cys Phe Arg Lys His Pro Asp
        195                 200                 205

Ala Thr Tyr Ser Arg Cys Gly Ser Gly Pro Trp Ile Thr Pro Arg Cys
    210                 215                 220

Leu Val Asp Tyr Pro Tyr Arg Leu Trp His Tyr Pro Cys Thr Ile Asn
225                 230                 235                 240
```

```
Tyr Thr Ile Phe Lys Ile Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Thr Thr Thr Gln
        275                 280                 285

Trp Gln Val Leu Pro Cys Ser Phe Thr Thr Leu Pro Ala Leu Ser Thr
290                 295                 300

Gly Leu Ile His Leu His Gln Asn Ile Val Asp Val Gln Tyr Leu Tyr
305                 310                 315                 320

Gly Val Gly Ser Ser
            325

<210> SEQ ID NO 7
<211> LENGTH: 446
<212> TYPE: PRT
<213> ORGANISM: Artificial Sequence
<220> FEATURE:
<223> OTHER INFORMATION: Synthetic peptide

<400> SEQUENCE: 7

Asp Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Arg Phe Thr Ile Ser Arg Asp Asn Ala Lys Asn Thr Leu Tyr
65                  70                  75                  80

Leu Gln Met Asn Ser Leu Arg Thr Glu Asp Thr Ala Leu Tyr Tyr Cys
                85                  90                  95

Thr Arg Gln Gly Tyr Gly Tyr Asn Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 8
<211> LENGTH: 218
<212> TYPE: PRT
<213> ORGANISM: Artificial Sequence
<220> FEATURE:
<223> OTHER INFORMATION: Synthetic peptide

<400> SEQUENCE: 8

Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Ala Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Ala Gly Val Tyr Tyr Cys Leu Gln Gly
                85                  90                  95

Ser His Val Pro Ser Thr Phe Gly Gly Gly Thr Lys Val Glu Ile Lys
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
         195                 200                 205

Val Thr Lys Ser Phe Asn Arg Gly Glu Cys
    210                 215

<210> SEQ ID NO 9
<211> LENGTH: 622
<212> TYPE: PRT
<213> ORGANISM: Artificial Sequence
<220> FEATURE:
<223> OTHER INFORMATION: Synthetic peptide

<400> SEQUENCE: 9

Tyr Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Met Thr Pro Thr Val Ala Thr Arg Asp Gly Lys Leu Pro Ala
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Gly
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Thr Ala Leu Val Met Ala
    130                 135                 140

Gln Leu Leu Arg Ile Pro Gln Ala Ile Leu Asp Met Ile Ala Gly Ala
145                 150                 155                 160

His Trp Gly Val Leu Ala Gly Gly Gly Ser Gly Gly Gly Gly Gly Ser
                165                 170                 175

Asp Val Gln Leu Leu Glu Ser Gly Gly Gly Leu Val Gln Pro Gly Gly
            180                 185                 190

Ser Leu Arg Leu Ser Cys Ala Ala Ser Gly Phe Asp Phe Ser Arg Tyr
        195                 200                 205

Trp Met Ser Trp Val Arg Gln Ala Pro Gly Lys Gly Leu Glu Trp Ile
    210                 215                 220

Gly Glu Ile Asn Pro Asp Ser Ser Thr Ile Asn Tyr Thr Pro Ser Leu
225                 230                 235                 240

Lys Asp Arg Phe Thr Ile Ser Arg Asp Asn Ala Lys Asn Thr Leu Tyr
                245                 250                 255

Leu Gln Met Asn Ser Leu Arg Thr Glu Asp Thr Ala Leu Tyr Tyr Cys
            260                 265                 270

Thr Arg Gln Gly Tyr Gly Tyr Asn Tyr Trp Gly Gln Gly Thr Thr Val
        275                 280                 285

Thr Val Ser Ser Ala Ser Thr Lys Gly Pro Ser Val Phe Pro Leu Ala
    290                 295                 300

Pro Ser Ser Lys Ser Thr Ser Gly Gly Thr Ala Ala Leu Gly Cys Leu
305                 310                 315                 320

Val Lys Asp Tyr Phe Pro Glu Pro Val Thr Val Ser Trp Asn Ser Gly
                325                 330                 335

Ala Leu Thr Ser Gly Val His Thr Phe Pro Ala Val Leu Gln Ser Ser
                340                 345                 350

Gly Leu Tyr Ser Leu Ser Ser Val Val Thr Val Pro Ser Ser Ser Leu
            355                 360                 365

Gly Thr Gln Thr Tyr Ile Cys Asn Val Asn His Lys Pro Ser Asn Thr
        370                 375                 380

Lys Val Asp Lys Lys Val Glu Pro Lys Ser Cys Asp Lys Thr His Thr
385                 390                 395                 400

Cys Pro Pro Cys Pro Ala Pro Glu Leu Leu Gly Gly Pro Ser Val Phe
                405                 410                 415

Leu Phe Pro Pro Lys Pro Lys Asp Thr Leu Met Ile Ser Arg Thr Pro
            420                 425                 430

Glu Val Thr Cys Val Val Val Asp Val Ser His Glu Asp Pro Glu Val
        435                 440                 445

Lys Phe Asn Trp Tyr Val Asp Gly Val Glu Val His Asn Ala Lys Thr
    450                 455                 460

Lys Pro Arg Glu Glu Gln Tyr Asn Ser Thr Tyr Arg Val Val Ser Val
465                 470                 475                 480

Leu Thr Val Leu His Gln Asp Trp Leu Asn Gly Lys Glu Tyr Lys Cys
                485                 490                 495

Lys Val Ser Asn Lys Ala Leu Pro Ala Pro Ile Glu Lys Thr Ile Ser
            500                 505                 510

Lys Ala Lys Gly Gln Pro Arg Glu Pro Gln Val Tyr Thr Leu Pro Pro
        515                 520                 525

Ser Arg Asp Glu Leu Thr Lys Asn Gln Val Ser Leu Thr Cys Leu Val
530                 535                 540

Lys Gly Phe Tyr Pro Ser Asp Ile Ala Val Glu Trp Glu Ser Asn Gly
545                 550                 555                 560

Gln Pro Glu Asn Asn Tyr Lys Thr Thr Pro Pro Val Leu Asp Ser Asp
                565                 570                 575

Gly Ser Phe Phe Leu Tyr Ser Lys Leu Thr Val Asp Lys Ser Arg Trp
            580                 585                 590

Gln Gln Gly Asn Val Phe Ser Cys Ser Val Met His Glu Ala Leu His
        595                 600                 605

Asn His Tyr Thr Gln Lys Ser Leu Ser Leu Ser Pro Gly Lys
    610                 615                 620

<210> SEQ ID NO 10
<211> LENGTH: 394
<212> TYPE: PRT
<213> ORGANISM: Artificial Sequence
<220> FEATURE:
<223> OTHER INFORMATION: Synthetic peptide

<400> SEQUENCE: 10

Tyr Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Met Thr Pro Thr Val Ala Thr Arg Asp Gly Lys Leu Pro Ala
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Gly
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Thr Ala Leu Val Met Ala
130                 135                 140

Gln Leu Leu Arg Ile Pro Gln Ala Ile Leu Asp Met Ile Ala Gly Ala
145                 150                 155                 160

His Trp Gly Val Leu Ala Gly Gly Gly Ser Gly Gly Gly Gly Ser
                165                 170                 175

Asp Val Leu Met Thr Gln Ser Pro Leu Ser Leu Pro Val Thr Leu Gly
                180                 185                 190

Gln Pro Ala Ser Ile Ser Cys Arg Ser Ser Gln Ser Ile Val His Ser
            195                 200                 205

Asn Gly Asn Thr Tyr Leu Glu Trp Tyr Leu Gln Lys Pro Gly Gln Ser
        210                 215                 220

Pro Lys Leu Leu Ile Tyr Lys Ala Ser Asn Arg Phe Ser Gly Val Pro
225                 230                 235                 240

Asp Arg Phe Ser Gly Ser Gly Ser Gly Thr Asp Phe Thr Leu Lys Ile
                245                 250                 255

Ser Arg Val Glu Ala Glu Asp Ala Gly Val Tyr Tyr Cys Leu Gln Gly
            260                 265                 270

Ser His Val Pro Ser Thr Phe Gly Gly Gly Thr Lys Val Glu Ile Lys
        275                 280                 285

Thr Val Ala Ala Pro Ser Val Phe Ile Phe Pro Pro Ser Asp Glu Gln
        290                 295                 300

Leu Lys Ser Gly Thr Ala Ser Val Val Cys Leu Leu Asn Asn Phe Tyr
305                 310                 315                 320

Pro Arg Glu Ala Lys Val Gln Trp Lys Val Asp Asn Ala Leu Gln Ser
                325                 330                 335

Gly Asn Ser Gln Glu Ser Val Thr Glu Gln Asp Ser Lys Asp Ser Thr
            340                 345                 350

Tyr Ser Leu Ser Ser Thr Leu Thr Leu Ser Lys Ala Asp Tyr Glu Lys
        355                 360                 365

His Lys Val Tyr Ala Cys Glu Val Thr His Gln Gly Leu Ser Ser Pro
    370                 375                 380

Val Thr Lys Ser Phe Asn Arg Gly Glu Cys
385                 390

<210> SEQ ID NO 11
<211> LENGTH: 781
<212> TYPE: PRT
<213> ORGANISM: Artificial Sequence
<220> FEATURE:
<223> OTHER INFORMATION: Synthetic peptide

<400> SEQUENCE: 11

Glu Thr His Val Thr Gly Gly Ser Ala Gly His Thr Ser Gly Phe
1               5                   10                  15

Val Ser Leu Leu Ala Pro Gly Ala Lys Gln Asn Val Gln Leu Ile Asn
            20                  25                  30

Thr Asn Gly Ser Trp His Leu Asn Ser Thr Ala Leu Asn Cys Asn Asp
        35                  40                  45

```
Ser Leu Asn Thr Gly Trp Leu Ala Gly Leu Phe Tyr His His Lys Phe
 50                  55                  60

Asn Ser Ser Gly Cys Pro Glu Arg Leu Ala Ser Cys Arg Pro Leu Thr
 65                  70                  75                  80

Asp Phe Asp Gln Gly Trp Gly Pro Ile Ser Tyr Ala Asn Gly Ser Gly
                 85                  90                  95

Pro Asp Gln Arg Pro Tyr Cys Trp His Tyr Pro Pro Lys Pro Cys Gly
            100                 105                 110

Ile Val Pro Ala Lys Ser Val Cys Gly Pro Val Tyr Cys Phe Thr Pro
            115                 120                 125

Ser Pro Val Val Val Gly Thr Thr Asp Arg Ser Gly Ala Pro Thr Tyr
130                 135                 140

Ser Trp Gly Glu Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Ala Gly
            180                 185                 190

Asn Asn Thr Leu His Cys Pro Thr Asp Cys Phe Arg Lys His Pro Asp
            195                 200                 205

Ala Thr Tyr Ser Arg Cys Gly Ser Gly Pro Trp Ile Thr Pro Arg Cys
            210                 215                 220

Leu Val Asp Tyr Pro Tyr Arg Leu Trp His Tyr Pro Cys Thr Ile Asn
225                 230                 235                 240

Tyr Thr Ile Phe Lys Ile Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Thr Thr Thr Gln
            275                 280                 285

Trp Gln Val Leu Pro Cys Ser Phe Thr Thr Leu Pro Ala Leu Ser Thr
            290                 295                 300

Gly Leu Ile His Leu His Gln Asn Ile Val Asp Val Gln Tyr Leu Tyr
305                 310                 315                 320

Gly Val Gly Ser Ser Gly Gly Gly Ser Gly Gly Gly Ser Asp
                325                 330                 335

Val Gln Leu Leu Glu Ser Gly Gly Leu Val Gln Pro Gly Gly Ser
            340                 345                 350

Leu Arg Leu Ser Cys Ala Ala Ser Gly Phe Asp Phe Ser Arg Tyr Trp
            355                 360                 365

Met Ser Trp Val Arg Gln Ala Pro Gly Lys Gly Leu Glu Trp Ile Gly
            370                 375                 380

Glu Ile Asn Pro Asp Ser Ser Thr Ile Asn Tyr Thr Pro Ser Leu Lys
385                 390                 395                 400

Asp Arg Phe Thr Ile Ser Arg Asp Asn Ala Lys Asn Thr Leu Tyr Leu
                405                 410                 415

Gln Met Asn Ser Leu Arg Thr Glu Asp Thr Ala Leu Tyr Tyr Cys Thr
            420                 425                 430

Arg Gln Gly Tyr Gly Tyr Asn Tyr Trp Gly Gln Gly Thr Thr Val Thr
            435                 440                 445

Val Ser Ser Ala Ser Thr Lys Gly Pro Ser Val Phe Pro Leu Ala Pro
450                 455                 460
```

Ser Ser Lys Ser Thr Ser Gly Gly Thr Ala Ala Leu Gly Cys Leu Val
465                 470                 475                 480

Lys Asp Tyr Phe Pro Glu Pro Val Thr Val Ser Trp Asn Ser Gly Ala
                485                 490                 495

Leu Thr Ser Gly Val His Thr Phe Pro Ala Val Leu Gln Ser Ser Gly
            500                 505                 510

Leu Tyr Ser Leu Ser Ser Val Val Thr Val Pro Ser Ser Ser Leu Gly
        515                 520                 525

Thr Gln Thr Tyr Ile Cys Asn Val Asn His Lys Pro Ser Asn Thr Lys
    530                 535                 540

Val Asp Lys Lys Val Glu Pro Lys Ser Cys Asp Lys Thr His Thr Cys
545                 550                 555                 560

Pro Pro Cys Pro Ala Pro Glu Leu Leu Gly Gly Pro Ser Val Phe Leu
                565                 570                 575

Phe Pro Pro Lys Pro Lys Asp Thr Leu Met Ile Ser Arg Thr Pro Glu
            580                 585                 590

Val Thr Cys Val Val Val Asp Val Ser His Glu Asp Pro Glu Val Lys
        595                 600                 605

Phe Asn Trp Tyr Val Asp Gly Val Glu Val His Asn Ala Lys Thr Lys
610                 615                 620

Pro Arg Glu Glu Gln Tyr Asn Ser Thr Tyr Arg Val Val Ser Val Leu
625                 630                 635                 640

Thr Val Leu His Gln Asp Trp Leu Asn Gly Lys Glu Tyr Lys Cys Lys
                645                 650                 655

Val Ser Asn Lys Ala Leu Pro Ala Pro Ile Glu Lys Thr Ile Ser Lys
            660                 665                 670

Ala Lys Gly Gln Pro Arg Glu Pro Gln Val Tyr Thr Leu Pro Pro Ser
        675                 680                 685

Arg Asp Glu Leu Thr Lys Asn Gln Val Ser Leu Thr Cys Leu Val Lys
690                 695                 700

Gly Phe Tyr Pro Ser Asp Ile Ala Val Glu Trp Glu Ser Asn Gly Gln
705                 710                 715                 720

Pro Glu Asn Asn Tyr Lys Thr Thr Pro Pro Val Leu Asp Ser Asp Gly
                725                 730                 735

Ser Phe Phe Leu Tyr Ser Lys Leu Thr Val Asp Lys Ser Arg Trp Gln
            740                 745                 750

Gln Gly Asn Val Phe Ser Cys Ser Val Met His Glu Ala Leu His Asn
        755                 760                 765

His Tyr Thr Gln Lys Ser Leu Ser Leu Ser Pro Gly Lys
770                 775                 780

<210> SEQ ID NO 12
<211> LENGTH: 553
<212> TYPE: PRT
<213> ORGANISM: Artificial Sequence
<220> FEATURE:
<223> OTHER INFORMATION: Synthetic peptide

<400> SEQUENCE: 12

Glu Thr His Val Thr Gly Gly Ser Ala Gly His Thr Val Ser Gly Phe
1               5                   10                  15

Val Ser Leu Leu Ala Pro Gly Ala Lys Gln Asn Val Gln Leu Ile Asn
            20                  25                  30

Thr Asn Gly Ser Trp His Leu Asn Ser Thr Ala Leu Asn Cys Asn Asp
        35                  40                  45

-continued

Ser Leu Asn Thr Gly Trp Leu Ala Gly Leu Phe Tyr His His Lys Phe
50                  55                  60

Asn Ser Ser Gly Cys Pro Glu Arg Leu Ala Ser Cys Arg Pro Leu Thr
65                  70                  75                  80

Asp Phe Asp Gln Gly Trp Gly Pro Ile Ser Tyr Ala Asn Gly Ser Gly
            85                  90                  95

Pro Asp Gln Arg Pro Tyr Cys Trp His Tyr Pro Pro Lys Pro Cys Gly
            100                 105                 110

Ile Val Pro Ala Lys Ser Val Cys Gly Pro Val Tyr Cys Phe Thr Pro
            115                 120                 125

Ser Pro Val Val Val Gly Thr Thr Asp Arg Ser Gly Ala Pro Thr Tyr
130                 135                 140

Ser Trp Gly Glu Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
            165                 170                 175

Phe Thr Lys Val Cys Gly Ala Pro Pro Cys Val Ile Gly Gly Ala Gly
            180                 185                 190

Asn Asn Thr Leu His Cys Pro Thr Asp Cys Phe Arg Lys His Pro Asp
            195                 200                 205

Ala Thr Tyr Ser Arg Cys Gly Ser Gly Pro Trp Ile Thr Pro Arg Cys
210                 215                 220

Leu Val Asp Tyr Pro Tyr Arg Leu Trp His Tyr Pro Cys Thr Ile Asn
225                 230                 235                 240

Tyr Thr Ile Phe Lys Ile Arg Met Tyr Val Gly Gly Val Glu His Arg
            245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Thr Thr Thr Gln
            275                 280                 285

Trp Gln Val Leu Pro Cys Ser Phe Thr Thr Leu Pro Ala Leu Ser Thr
290                 295                 300

Gly Leu Ile His Leu His Gln Asn Ile Val Asp Val Gln Tyr Leu Tyr
305                 310                 315                 320

Gly Val Gly Ser Ser Gly Gly Gly Ser Gly Gly Gly Ser Asp
            325                 330                 335

Val Leu Met Thr Gln Ser Pro Leu Ser Leu Pro Val Thr Leu Gly Gln
            340                 345                 350

Pro Ala Ser Ile Ser Cys Arg Ser Ser Gln Ser Ile Val His Ser Asn
            355                 360                 365

Gly Asn Thr Tyr Leu Glu Trp Tyr Leu Gln Lys Pro Gly Gln Ser Pro
370                 375                 380

Lys Leu Leu Ile Tyr Lys Ala Ser Asn Arg Phe Ser Gly Val Pro Asp
385                 390                 395                 400

Arg Phe Ser Gly Ser Gly Ser Gly Thr Asp Phe Thr Leu Lys Ile Ser
            405                 410                 415

Arg Val Glu Ala Glu Asp Ala Gly Val Tyr Tyr Cys Leu Gln Gly Ser
            420                 425                 430

His Val Pro Ser Thr Phe Gly Gly Gly Thr Lys Val Glu Ile Lys Thr
            435                 440                 445

Val Ala Ala Pro Ser Val Phe Ile Phe Pro Pro Ser Asp Glu Gln Leu
450                 455                 460

Lys Ser Gly Thr Ala Ser Val Val Cys Leu Leu Asn Asn Phe Tyr Pro

```
           465                 470                 475                 480
Arg Glu Ala Lys Val Gln Trp Lys Val Asp Asn Ala Leu Gln Ser Gly
                    485                 490                 495

Asn Ser Gln Glu Ser Val Thr Glu Gln Asp Ser Lys Asp Ser Thr Tyr
            500                 505                 510

Ser Leu Ser Ser Thr Leu Thr Leu Ser Lys Ala Asp Tyr Glu Lys His
            515                 520                 525

Lys Val Tyr Ala Cys Glu Val Thr His Gln Gly Leu Ser Ser Pro Val
            530                 535                 540

Thr Lys Ser Phe Asn Arg Gly Glu Cys
545                 550

<210> SEQ ID NO 13
<211> LENGTH: 813
<212> TYPE: PRT
<213> ORGANISM: Artificial Sequence
<220> FEATURE:
<223> OTHER INFORMATION: Synthetic peptide

<400> SEQUENCE: 13

Met Val Gly Asn Trp Ala Lys Val Leu Val Leu Leu Leu Phe Ala
1               5                   10                  15

Gly Val Asp Ala Glu Thr His Val Thr Gly Gly Ser Ala Gly His Thr
                20                  25                  30

Val Ser Gly Phe Val Ser Leu Leu Ala Pro Gly Ala Lys Gln Asn Val
            35                  40                  45

Gln Leu Ile Asn Thr Asn Gly Ser Trp His Leu Asn Ser Thr Ala Leu
    50                  55                  60

Asn Cys Asn Asp Ser Leu Asn Thr Gly Trp Leu Ala Gly Leu Phe Tyr
65                  70                  75                  80

His His Lys Phe Asn Ser Ser Gly Cys Pro Glu Arg Leu Ala Ser Cys
                85                  90                  95

Arg Pro Leu Thr Asp Phe Asp Gln Gly Trp Gly Pro Ile Ser Tyr Ala
            100                 105                 110

Asn Gly Ser Gly Pro Asp Gln Arg Pro Tyr Cys Trp His Tyr Pro Pro
        115                 120                 125

Lys Pro Cys Gly Ile Val Pro Ala Lys Ser Val Cys Gly Pro Val Tyr
    130                 135                 140

Cys Phe Thr Pro Ser Pro Val Val Val Gly Thr Thr Asp Arg Ser Gly
145                 150                 155                 160

Ala Pro Thr Tyr Ser Trp Gly Glu Asn Asp Thr Asp Val Phe Val Leu
                165                 170                 175

Asn Asn Thr Arg Pro Pro Leu Gly Asn Trp Phe Gly Cys Thr Trp Met
            180                 185                 190

Asn Ser Thr Gly Phe Thr Lys Val Cys Gly Ala Pro Pro Cys Val Ile
        195                 200                 205

Gly Gly Ala Gly Asn Asn Thr Leu His Cys Pro Thr Asp Cys Phe Arg
    210                 215                 220

Lys His Pro Asp Ala Thr Tyr Ser Arg Cys Gly Ser Gly Pro Trp Ile
225                 230                 235                 240

Thr Pro Arg Cys Leu Val Asp Tyr Pro Tyr Arg Leu Trp His Tyr Pro
                245                 250                 255

Cys Thr Ile Asn Tyr Thr Ile Phe Lys Ile Arg Met Tyr Val Gly Gly
            260                 265                 270

Val Glu His Arg Leu Glu Ala Ala Cys Asn Trp Thr Arg Gly Glu Arg
```

```
            275                 280                 285
Cys Asp Leu Glu Asp Arg Asp Arg Ser Glu Leu Ser Pro Leu Leu Leu
    290                 295                 300
Thr Thr Thr Gln Trp Gln Val Leu Pro Cys Ser Phe Thr Thr Leu Pro
305                 310                 315                 320
Ala Leu Ser Thr Gly Leu Ile His Leu His Gln Asn Ile Val Asp Val
                325                 330                 335
Gln Tyr Leu Tyr Gly Val Gly Ser Ser Gly Gly His His His
                340                 345                 350
His His His Ile Glu Gly Arg Gly Ser Asp Val Gln Leu Leu Glu Ser
            355                 360                 365
Gly Gly Gly Leu Val Gln Pro Gly Gly Ser Leu Arg Leu Ser Cys Ala
    370                 375                 380
Ala Ser Gly Phe Asp Phe Ser Arg Tyr Trp Met Ser Trp Val Arg Gln
385                 390                 395                 400
Ala Pro Gly Lys Gly Leu Glu Trp Ile Gly Glu Ile Asn Pro Asp Ser
                405                 410                 415
Ser Thr Ile Asn Tyr Thr Pro Ser Leu Lys Asp Arg Phe Thr Ile Ser
                420                 425                 430
Arg Asp Asn Ala Lys Asn Thr Leu Tyr Leu Gln Met Asn Ser Leu Arg
            435                 440                 445
Thr Glu Asp Thr Ala Leu Tyr Tyr Cys Thr Arg Gln Gly Tyr Gly Tyr
    450                 455                 460
Asn Tyr Trp Gly Gln Gly Thr Thr Val Thr Val Ser Ser Ala Ser Thr
465                 470                 475                 480
Lys Gly Pro Ser Val Phe Pro Leu Ala Pro Ser Ser Lys Ser Thr Ser
                485                 490                 495
Gly Gly Thr Ala Ala Leu Gly Cys Leu Val Lys Asp Tyr Phe Pro Glu
                500                 505                 510
Pro Val Thr Val Ser Trp Asn Ser Gly Ala Leu Thr Ser Gly Val His
            515                 520                 525
Thr Phe Pro Ala Val Leu Gln Ser Ser Gly Leu Tyr Ser Leu Ser Ser
    530                 535                 540
Val Val Thr Val Pro Ser Ser Ser Leu Gly Thr Gln Thr Tyr Ile Cys
545                 550                 555                 560
Asn Val Asn His Lys Pro Ser Asn Thr Lys Val Asp Lys Lys Val Glu
                565                 570                 575
Pro Lys Ser Cys Asp Lys Thr His Thr Cys Pro Pro Cys Pro Ala Pro
                580                 585                 590
Glu Leu Leu Gly Gly Pro Ser Val Phe Leu Phe Pro Pro Lys Pro Lys
            595                 600                 605
Asp Thr Leu Met Ile Ser Arg Thr Pro Glu Val Thr Cys Val Val Val
    610                 615                 620
Asp Val Ser His Glu Asp Pro Glu Val Lys Phe Asn Trp Tyr Val Asp
625                 630                 635                 640
Gly Val Glu Val His Asn Ala Lys Thr Lys Pro Arg Glu Glu Gln Tyr
                645                 650                 655
Asn Ser Thr Tyr Arg Val Val Ser Val Leu Thr Val Leu His Gln Asp
                660                 665                 670
Trp Leu Asn Gly Lys Glu Tyr Lys Cys Lys Val Ser Asn Lys Ala Leu
            675                 680                 685
Pro Ala Pro Ile Glu Lys Thr Ile Ser Lys Ala Lys Gly Gln Pro Arg
    690                 695                 700
```

Glu Pro Gln Val Tyr Thr Leu Pro Pro Ser Arg Asp Glu Leu Thr Lys
705                 710                 715                 720

Asn Gln Val Ser Leu Thr Cys Leu Val Lys Gly Phe Tyr Pro Ser Asp
            725                 730                 735

Ile Ala Val Glu Trp Glu Ser Asn Gly Gln Pro Glu Asn Asn Tyr Lys
        740                 745                 750

Thr Thr Pro Pro Val Leu Asp Ser Asp Gly Ser Phe Phe Leu Tyr Ser
    755                 760                 765

Lys Leu Thr Val Asp Lys Ser Arg Trp Gln Gln Gly Asn Val Phe Ser
770                 775                 780

Cys Ser Val Met His Glu Ala Leu His Asn His Tyr Thr Gln Lys Ser
785                 790                 795                 800

Leu Ser Leu Ser Pro Gly Lys Ser Glu Lys Asp Glu Leu
            805                 810

<210> SEQ ID NO 14
<211> LENGTH: 31
<212> TYPE: DNA
<213> ORGANISM: Artificial Sequence
<220> FEATURE:
<223> OTHER INFORMATION: Synthetic primer

<400> SEQUENCE: 14
atcgtctaga accatggtgc gctcctccaa g                          31

<210> SEQ ID NO 15
<211> LENGTH: 28
<212> TYPE: DNA
<213> ORGANISM: Artificial Sequence
<220> FEATURE:
<223> OTHER INFORMATION: Synthetic primer

<400> SEQUENCE: 15
attagagctc ctacaggaac aggtggtg                              28

<210> SEQ ID NO 16
<211> LENGTH: 28
<212> TYPE: DNA
<213> ORGANISM: Artificial Sequence
<220> FEATURE:
<223> OTHER INFORMATION: Synthetic primer

<400> SEQUENCE: 16
tgacctgcag gcatggtgga gcacgaca                              28

<210> SEQ ID NO 17
<211> LENGTH: 26
<212> TYPE: DNA
<213> ORGANISM: Artificial Sequence
<220> FEATURE:
<223> OTHER INFORMATION: Synthetic primer

<400> SEQUENCE: 17
tgaatagtgc atatcagcat acctta                                26

<210> SEQ ID NO 18
<211> LENGTH: 50
<212> TYPE: DNA
<213> ORGANISM: Artificial Sequence
<220> FEATURE:
<223> OTHER INFORMATION: Synthetic primer

<400> SEQUENCE: 18
gcggtacctt aaagctcatc cttctctgat ttacccggag acaaggagag        50

<210> SEQ ID NO 19
<211> LENGTH: 31
<212> TYPE: DNA
<213> ORGANISM: Artificial Sequence
<220> FEATURE:
<223> OTHER INFORMATION: Synthetic primer

<400> SEQUENCE: 19
acgatctaga acaatgggat ggtcttgcat c        31

<210> SEQ ID NO 20
<211> LENGTH: 24
<212> TYPE: DNA
<213> ORGANISM: Artificial Sequence
<220> FEATURE:
<223> OTHER INFORMATION: Synthetic primer

<400> SEQUENCE: 20
gtcaccatgg tgagcaaggg cgag        24

<210> SEQ ID NO 21
<211> LENGTH: 28
<212> TYPE: DNA
<213> ORGANISM: Artificial Sequence
<220> FEATURE:
<223> OTHER INFORMATION: Synthetic primer

<400> SEQUENCE: 21
ctcaggatcc ttacttgtac agctcgtc        28

<210> SEQ ID NO 22
<211> LENGTH: 31
<212> TYPE: DNA
<213> ORGANISM: Artificial Sequence
<220> FEATURE:
<223> OTHER INFORMATION: Synthetic primer

<400> SEQUENCE: 22
atcgtctaga accatggtgc gctcctccaa g        31

<210> SEQ ID NO 23
<211> LENGTH: 28
<212> TYPE: DNA
<213> ORGANISM: Artificial Sequence
<220> FEATURE:
<223> OTHER INFORMATION: Synthetic primer

<400> SEQUENCE: 23
attagagctc ctacaggaac aggtggtg        28

<210> SEQ ID NO 24
<211> LENGTH: 48
<212> TYPE: DNA
<213> ORGANISM: Artificial Sequence
<220> FEATURE:
<223> OTHER INFORMATION: Synthetic primer

<400> SEQUENCE: 24
ccaggatccg ccacctcctg atccacctcc gcctgcaagg actcccca        48

<210> SEQ ID NO 25
<211> LENGTH: 29
<212> TYPE: DNA

```
<213> ORGANISM: Artificial Sequence
<220> FEATURE:
<223> OTHER INFORMATION: Synthetic primer

<400> SEQUENCE: 25
ttggctcgag tatttttaca acaattacc                                    29

<210> SEQ ID NO 26
<211> LENGTH: 30
<212> TYPE: DNA
<213> ORGANISM: Artificial Sequence
<220> FEATURE:
<223> OTHER INFORMATION: Synthetic primer

<400> SEQUENCE: 26
gtcggatccg atgttttgat gactcaaagc                                   30

<210> SEQ ID NO 27
<211> LENGTH: 26
<212> TYPE: DNA
<213> ORGANISM: Artificial Sequence
<220> FEATURE:
<223> OTHER INFORMATION: Synthetic primer

<400> SEQUENCE: 27
tgaatagtgc atatcagcat acctta                                       26

<210> SEQ ID NO 28
<211> LENGTH: 52
<212> TYPE: DNA
<213> ORGANISM: Artificial Sequence
<220> FEATURE:
<223> OTHER INFORMATION: Synthetic primer

<400> SEQUENCE: 28
aacggatcca cctccacctg atccacctcc accacttgat cccacaccgt ac          52

<210> SEQ ID NO 29
<211> LENGTH: 24
<212> TYPE: DNA
<213> ORGANISM: Artificial Sequence
<220> FEATURE:
<223> OTHER INFORMATION: Synthetic primer

<400> SEQUENCE: 29
caagcattct acttctattg cagc                                         24

<210> SEQ ID NO 30
<211> LENGTH: 34
<212> TYPE: DNA
<213> ORGANISM: Artificial Sequence
<220> FEATURE:
<223> OTHER INFORMATION: Synthetic primer

<400> SEQUENCE: 30
gtcggatccg atgttcagct tcttgagtct ggag                              34

<210> SEQ ID NO 31
<211> LENGTH: 26
<212> TYPE: DNA
<213> ORGANISM: Artificial Sequence
<220> FEATURE:
<223> OTHER INFORMATION: Synthetic primer

<400> SEQUENCE: 31
tgaatagtgc atatcagcat acctta                                       26
```

<210> SEQ ID NO 32
<211> LENGTH: 469
<212> TYPE: PRT
<213> ORGANISM: Artificial Sequence
<220> FEATURE:
<223> OTHER INFORMATION: Synthetic peptide

<400> SEQUENCE: 32

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
                20                  25                  30

Ser Val Gly Leu Asn Leu Glu Gly Asn Gly Val Ala Thr Asp Val Pro
            35                  40                  45

Ser Ala Thr Lys Arg Trp Gly Phe Arg Ser Gly Val Pro Pro Lys Val
        50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285

Gln Ser Pro Ala Arg Thr Ser Ser Asp Pro Gly Thr Asn Thr Thr Thr
    290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
            340                 345                 350

Asp Asn Ser Thr His Asn Thr Pro Val Tyr Lys Leu Asp Ile Ser Glu
        355                 360                 365
```

```
Ala Thr Gln Val Glu Gln His His Arg Arg Thr Asp Asn Asp Ser Thr
        370                 375                 380

Ala Ser Asp Thr Pro Ser Ala Thr Thr Ala Ala Gly Pro Pro Lys Ala
385                 390                 395                 400

Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
            420                 425                 430

His His Gln Asp Thr Gly Glu Glu Ser Ala Ser Ser Gly Lys Leu Gly
        435                 440                 445

Leu Ile Thr Asn Thr Ile Ala Gly Val Ala Gly Leu Ile Thr Gly Gly
    450                 455                 460

Arg Arg Thr Arg Arg
465

<210> SEQ ID NO 33
<211> LENGTH: 22
<212> TYPE: DNA
<213> ORGANISM: Artificial Sequence
<220> FEATURE:
<223> OTHER INFORMATION: Synthetic primer

<400> SEQUENCE: 33
cacctcaccc atcttttatt ac                                          22

<210> SEQ ID NO 34
<211> LENGTH: 44
<212> TYPE: DNA
<213> ORGANISM: Artificial Sequence
<220> FEATURE:
<223> OTHER INFORMATION: Synthetic primer

<400> SEQUENCE: 34
cgggatccac ctccaccaga tccacctcca cctgtgatca ggcc                  44

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide

<400> SEQUENCE: 35

Gly Gly Ser Gly Gly Gly Ser
1               5

<210> SEQ ID NO 36
<211> LENGTH: 19
<212> TYPE: PRT
<213> ORGANISM: Artificial Sequence
<220> FEATURE:
<223> OTHER INFORMATION: Synthetic peptide

<400> SEQUENCE: 36

Met Gly Trp Ser Cys Ile Ile Leu Phe Leu Val Ala Thr Ala Thr Gly
1               5                   10                  15

Val His Ser

<210> SEQ ID NO 37
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 37

Gly Gly Gly Ser Gly Gly Gly Ser
1               5

<210> SEQ ID NO 38
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 38

Lys Asp Glu Leu
1

<210> SEQ ID NO 39
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 39

Ser Glu Lys Asp Gly Leu
1               5
```

METHODS AND COMPOSITIONS RELATED TO GLYCOPROTEIN-IMMUNOGLOBULIN FUSIONS

This application is a national phase application under 35 U.S.C. § 371 of International Application No. PCT/US2011/024466 filed Feb. 11, 2011, which claims priority to U.S. Provisional Patent Application serial number 61/304,178 filed Feb. 12, 2010, the entire contents of each of which is incorporated herein by reference in its entirety.

This invention was made with government support under U19-AI-066332 awarded by the National Institutes of Health. The government has certain rights in the invention.

BACKGROUND OF THE INVENTION

I. Field of the Invention

Embodiments of this invention are directed generally to biology, medicine, and immunology. Certain aspects are directed to glycoprotein-immunoglobulin fusion proteins.

II. Background

Stable transgenic plants have been used to produce a variety of non-plant proteins. One use of stable transgenic plants is the production of virus-like particles (VLPs) for use in vaccines. VLP-forming antigens of different origins expressed in transgenic plants have been shown to assemble into VLPs, and their immunogenicity have been demonstrated in experimental animals when delivered by injection of purified forms or by oral consumption of unprocessed plant tissues (reviewed in Santi et al., 2006; Thanavala et al., 2006). Phase I clinical trials using transgenic plant-derived hepatitis B surface antigen (HBsAg) and Norwalk virus capsid protein (NVCP) VLPs showed safety and oral immunogenicity in humans (Tacket et al., 2000; Thanavala et al., 2005). However, long generation time and modest levels of antigen accumulation (<1% total soluble protein or <0.1 mg/g fresh weight) are two main factors limiting the practical application of transgenic plants for commercial production of VLPs.

Plant virus-based transient expression has the potential of achieving high-level antigen accumulation in a short period of time (≤2 weeks) (reviewed in Canizares et al., 2005; Gleba et al., 2007; Lico et al., 2008; Yusibov et al., 2006). However, the difficulty in genetic manipulation of large full-length or near-full-length viral genomes and inconvenient infection procedures, which some times involve in vitro transcription of DNA to infectious RNA and the co-delivery of multiple DNA/RNA segments, represent major challenges in commercial application of this technology. For example, even the new generation tobacco mosaic virus (TMV)-based "deconstructed" vector system, requires simultaneous cointroduction of three vector modules into same cells for in planta assembly of the RNA replicon (Marillonnet et al., 2004). Thus, further development of simple, easily manipulated viral vectors (e.g., vectors to produce vaccine antigens and the like) is warranted. Such technology, and the products of using such technology, would provide additional compositions and methods for producing and using glycoprotein antigens for therapy and vaccination.

The need for further development of these technologies is exemplified by the need for additional compositions and methods for treating Hepatitis C virus (HCV) infections. More than 170 million people worldwide are chronic carriers of HCV (Delwaide et al. 2000). There is neither a prophylactic nor a therapeutic vaccine currently available for HCV. The route of infection is via blood and other body fluids and over 70% of patients become chronic carriers of the virus. Persistent infection results in chronic active hepatitis which may lead to progressive liver disease (Alter et al., 1999). Presently, the only therapy for hepatitis C infection is interferon-α (IFN-α) and Ribavirin. However, this therapy is expensive, has substantial side effects, and is effective in only approximately 50% of a selected group of patients. Therapeutic vaccines that enhance host immune responses to eliminate chronic HCV infection will be a major advancement in the treatment of this disease.

The immune system plays a key role in the outcome of an HCV infection. Most individuals that are exposed to HCV mount a broad strong and multi-antigen-specific CD4+ (regulatory) and CD8+ (cytotoxic) T cell response to the virus. These individuals develop only a self-limited infection. However, in some individuals exposed to HCV, a weak or undetectable and narrowly focused immune response results in chronic infection.

There is a need for additional therapies for infections such as HCV. Therapies can include vaccines that target heteromeric glycoproteins from a variety of animals, plants and microbes; particularly those therapies that enhance or induce immune responses to viruses that produce heterodimeric envelope proteins.

SUMMARY OF THE INVENTION

Disclosed herein are compositions and methods for eliciting immune responses against a heterodimeric glycoprotein of animals, plants, or microbes. In certain aspects the heterodimeric glycoproteins are viral heterodimeric glycoproteins, such as those produced by Hepatitis C virus (HCV), Rubella virus, Varicella-Zoster virus, Rift Valley Fever virus, and other members of the Flaviviridae, Togoviridae, Herpesviridae, or Bunyaviridae family. In particular embodiments, the compounds and methods are directed to all or a segment of HCV glycoprotein E1 and/or HCV glycoprotein E2.

Compositions of the invention are recombinant glycoproteins produced as fusion proteins of selected glycoproteins and specific antibody regions. The compositions present a heterodimeric glycoprotein that form a tetramer as schematically represented in FIG. 1. The polypeptide complexes comprise two fusion proteins, a first fusion protein comprises an immunoglobulin light chain polypeptide coupled to a first glycoprotein or segment thereof, for example an HCV E1 or E2 glycoprotein. The second fusion protein comprises an immunoglobulin heavy chain polypeptide coupled to a second glycoprotein or segment thereof, for example an HCV E1 or E2 glycoprotein. The first and second fusion proteins associate to form a heterodimer that further associates to form a tetramer comprising two heterodimers. In certain embodiments, the glycoproteins or glycoprotein segments are derived from HCV.

In other aspects, the immunoglobulin polypeptide segments are derived from polypeptides that comprise antibody constant regions. Conventional antibodies are large multi-subunit protein molecules comprising at least four polypeptide chains. For example, human IgG has two heavy chains and two light chains that are disulfide bonded to form the functional antibody. The size of a conventional IgG is about 150 kD. The heavy and light polypeptide chains of antibodies comprise variable (V) regions that directly participate in antigen interactions, and constant (C) regions that provide structural support and function in non-antigen-specific interactions with immune effectors. In vivo, a diverse primary repertoire of V genes that encode the $V_H$ and $V_L$ domains is produced by the combinatorial rearrangement of gene segments. C regions include the light chain C regions (referred to as $C_L$ regions) and the heavy chain C regions (referred to as $CH_1$, $CH_2$ and $CH_3$ regions).

Certain embodiments of the invention are directed to polypepide compositions comprising a first polypeptide comprising a carboxy terminal immunoglobulin heavy chain polypeptide and an amino terminal first glycoprotein polypeptide; and a second polypeptide comprising a carboxy terminal light chain immunoglobulin polypeptide and an amino terminal second glycoprotein polypeptide, wherein the first and second glycoprotein is in a complex forming at least one heterodimeric glycoprotein. In certain aspects, the first glycoprotein polypeptide is a first viral glycoprotein polypeptide, and the second glycoprotein polypeptide is a second viral glycoprotein. The first and second viral glycoproteins can be Flaviviridae, Togoviridae, Herpesviridae, or Bunyaviridae glycoproteins. In a further aspect, the glycoproteins are Hepatitis C, Rubella, Varicella-Zoster, or Rift Valley Fever virus glycoproteins. In still a further aspect the glycoproteins are Hepatitis C virus glycoproteins, such as an HCV E1 or E2 glycoprotein and the second glycoprotein is an HCV E2 or E1 glycoprotein. In certain aspects, the first and second viral glycoprotein assemble to form an HCVE1/E2 glycoprotein complex. The HCV E1 glycoprotein segment can comprise an amino acid sequence that is at least 80, 85, 90, 95, 98, 99, or 100% identical to all or part of SEQ ID NO:4. The carboxy terminal immunoglobulin heavy chain polypeptide can comprise an amino acid sequence that is at least 80, 85, 90, 95, 98, 99, 100% identical to all or part of SEQ ID NO:9 or SEQ ID NO:11. The HCV E2 glycoprotein segment comprises an amino acid sequence that is at least 80, 85, 90, 95, 98, 99, 100% identical to all or part of SEQ ID NO:6. The carboxy terminal immunoglobulin light chain polypeptide can comprise an amino acid sequence that is at least 80, 85, 90, 95, 98, 99, 100% identical to all or part SEQ ID NO: 10 or SEQ ID NO:12. The composition can further comprise a polypeptide tetramer comprising two first polypeptides and two second polypeptides. In certain aspects, the first polypeptide and/or the second polypeptide can further comprise one or more of a histidine tag and/or a protease cleavage site, as well as a trafficking signal or leader sequence and/or a endoplasmic reticulum retention sequence.

Other embodiments are directed to a protein complex produced by a method comprising: (a) obtaining plant cells expressing both a first polypeptide comprising, from a carboxy terminus to amino terminus, an immunoglobulin heavy chain segment fused to a first glycoprotein segment, and a second polypeptide comprising, from a carboxy terminus to amino terminus, an immunoglobulin light chain segment fused to a second glycoprotein segment, and/or (b) isolating a protein complex comprising the first polypeptide and second polypeptide from the plant tissue.

Further embodiments include methods of producing a protein complex comprising: (a) expressing in a plant cell (i) a first polypeptide comprising, from a carboxy terminus to amino terminus, an immunoglobulin heavy chain segment fused to a first glycoprotein segment encoded by a first polypeptide encoding segment, and (ii) a second polypeptide comprising, from a carboxy terminus to amino terminus, an immunoglobulin light chain segment fused to second glycoprotein segment encoded by a second polypeptide encoding segment; and/or (b) isolating a protein complex comprising the first polypeptide and second polypeptide from the plant cell. In certain aspects the plant cell is a Nicotiana benthamiana cell. In certain aspects, the first polypeptide encoding segment and the second polypeptide encoding segment are encoded in a single vector. In a further aspect, the single vector comprises a nucleic acid segment that encodes the Rep/RepA protein of a geminivirus. Certain embodiments are directed to a polynucleotide encoding the first and second polypeptides described herein. In certain aspects the first polypeptide encoding segment and the second polypeptide encoding segment are each flanked by at least a portion of a geminivirus long intergenic region. Certain aspects include a vector comprising a polynucleotide described herein. The vector can be a single geminivirus expression vector comprising the first polypeptide encoding segment, the second polypeptide encoding segment, and a geminivirus Rep/Rep A polypeptide encoding segment.

Other embodiments include host cells comprising a polynucleotide as described herein. In certain aspects the host cell is a plant or plant cell.

Embodiments are also directed to methods of treating a subject having an HCV infection comprising administering an effective amount of a protein complex comprising a first polypeptide comprising from a carboxy terminus to amino terminus an immunoglobulin heavy chain segment fused to an HCV E1 glycoprotein segment or HCV E2 glycoprotein segment, and a second polypeptide comprising from a carboxy terminus to amino terminus an immunoglobulin light chain segment fused to an HCV E1 glycoprotein segment or HCV E2 glycoprotein segment.

Further embodiments include methods of treating a subject at risk of acquiring an HCV infection comprising administering an effective amount of a protein complex comprising a first polypeptide comprising from a carboxy terminus to amino terminus an immunoglobulin heavy chain segment fused to an HCV E1 glycoprotein segment or HCV E2 glycoprotein segment, and a second polypeptide comprising from a carboxy terminus to amino terminus an immunoglobulin light chain segment fused to an HCV E1 glycoprotein segment or HCV E2 glycoprotein segment.

As used herein, the term "antigen" is a molecule capable of inducing a humoral immune response and/or cellular immune response leading to the production of B- and/or T-lymphocytes. The structural aspect of an antigen that gives rise to a biological response is referred to herein as an "antigenic determinant." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another.

Certain aspects relate to antigen presentation and/or immune modulation using protein complex to stimulate dendritic cells or other antigen presenting cells. In various aspects, methods comprise administering an HCV protein complex to the subject. In various other embodiments, the amount is effective to promote dendritic cell maturation. In various aspects the subject is a mammal, such as a human.

Dendritic cells ("DC") are one type of antigen-presenting cell ("APC") of the immune system. Dendritic cells typically ingest antigens by phagocytosis, pinocytosis, or via interaction with a variety of cell surface receptors and endocytosis; degrade the antigens; then present fragments of those antigens in association with MHC ("major histocompatibility complex") on their surfaces that other immune cells (primarily T cells) bind. Dendritic cells can be characterized by long "dendritic" processes (resembling dendrites in nerve cells). These cells are typically found in nonlymphoid organs, for example, the skin (where they are called Langerhans cells), nose, heart, liver, kidneys, lungs, stomach, intestines, etc., where they are able to capture antigens. It is believed that, upon capturing antigens, dendritic cells migrate through the circulation (blood and lymph) to the lymphoid organs where they can interact with T cells to induce their proliferation, activation to effectors, activation to memory, deletion (death), anergy (inactivation) or regulatory functions.

"Antibody" refers to an immunoglobulin molecule produced by B lymphoid cells. These molecules are characterized by having the ability to bind specifically with an antigen, each being defined in terms of the other.

"Antibody response" or "humoral response" refers to a type of immune response in which antibodies are produced by B lymphocytes and are secreted into the blood and/or lymph in response to an antigenic stimulus. In a properly functioning immune response, the antibody binds specifically to antigens on the surface of cells (e.g., a pathogen), marking the cell for destruction by phagocytic cells, antibody-dependent cellular cytotoxicity (ADCC) effector cells, and/or complement-mediated mechanisms. Antibodies also circulate systemically and can bind to free virions. This antibody binding can neutralize the virion and prevent it from infecting a cell as well as marking the virion for elimination from host by phagocytosis or filtration in the kidneys.

"Cellular response" or "cellular host response" refers to a type of immune response mediated by helper and killer T cells capable of directly or indirectly eliminating virally infected or cancerous cells.

"Immunity" or "immune response" refers to the body's response to an antigen. In particular embodiments, it refers to the ability of the body to resist or protect itself against infectious disease.

As used herein, "prophylaxis" means complete prevention of the symptoms of a disease, a delay in onset of the symptoms of a disease, or a lessening in the severity of subsequently developed disease symptoms.

"Prevention" of a disease means that symptoms of the disease are essentially absent.

The phrase "therapeutically effective amount" refers to an amount of an agent sufficient to elicit an effective B cell, cytotoxic T lymphocyte (CTL) and/or helper T lymphocyte (Th) response to the antigen and to block or to cure or at least partially arrest or slow symptoms and/or complications of a disease or disorder.

The terms "treating" and "treatment" as used herein cover any treatment of a condition treatable by a immunogenic composition described herein in an animal, particularly a human, and include: (i) preventing the condition or symptoms of the conditions from occurring in a subject predisposed to the condition but not yet been diagnosed; (ii) inhibiting the condition, e.g., arresting or slowing its development; or (iii) relieving the condition, e.g., causing regression of the condition or its symptoms.

The terms "inhibiting," "reducing," or "prevention," or any variation of these terms, when used in the claims and/or the specification includes any measurable decrease of a symptom of a disease or condition in achieving a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 9. Expression of Ebola GP1-Ig H-chain fusion protein (gp1dH2) either with or without the light chain (K3) shows accumulation of high-molecular weight proteins reactive with both anti-H chain (left) and anti-GP1 (right) antibodies.

FIG. 10. Guinea pig anti-gpE1/E2 scrum reactive proteins from leaves co-expressing gpE2 fusions with heavy chain (gamma) or light chain (kappa) proteins.

DETAILED DESCRIPTION OF THE INVENTION

Disclosed herein are compositions and methods related to heterodimeric glycoproteins. In particular embodiments, the compositions and methods are related to eliciting immune responses against all or a segment of heterodimeric glycoproteins or viral heterodimeric glycoproteins. In certain aspects the compositions and methods are related to producing tetrameric complexes and/or eliciting immune responses to the E1/E2 glycoprotein of HCV.

I. Heterodimeric Glycoproteins

Heterodimeric glycoproteins are produced by a variety of organisms including animals, plants, and microbes. The term "heterodimeric" indicates that two distinct polypeptides or peptides (heterologous polypeptides or peptides) associate to form a dimeric or two component protein complex. Glycoproteins are proteins that contain oligosaccharide chains (glycans) attached to amino acid side chains of a polypeptide or peptide.

A. Viral Envelope Proteins

Aspects of the invention include heterodimeric complexes of viral glycoproteins. Viral glycoproteins are produced by a number of viruses in the Flaviviridae, Togaviridae, Herpesviridae and Bunyaviridae families. Viral heterodimeric glycoproteins typically function to bind target cells by interacting with proteins on a target cell's surface.

HCV is a member of the Flaviviridae family which can infect humans, resulting in acute and chronic hepatitis, and may result in hepatocellular carcinoma (Hoofnagle, 2002). The HCV genome is a 9.6 Kb uncapped positive polarity single stranded RNA molecule and the replication occurs via a negative-strand intermediate (Lindenbach and Rice, 2005). The HCV genome encodes a single open reading frame that encodes a polyprotein, which is processed to generate the core or capsid protein (C), two envelope glycoproteins (E1 & E2), a small hydrophobic protein (p7), and six non-structural proteins (NS2, NS3, NS4A, NS4B, NS5A & NS5B). The processing of the polyprotein into the individual proteins is catalyzed by host and viral proteases (Lohmann et al., 1996; Penin et al., 2004). The absence of vigorous response against HCV antigens results in chronic infection Certain compositions of the invention are recombinant glycoproteins produced as fusion proteins of a glycoprotein or segment thereof and an immunoglobulin segment. For example, the compositions can include heterodimeric glycoproteins that can form a tetrameric complex (2 E1 antigens and 2 E2 antigens), as schematically represented in FIG. 1. The recombinant glycoprotein can comprise two fusion proteins, a first fusion protein comprising, from a carboxy to amino terminal direction, an immunoglobulin light chain polypeptide coupled to a first glycoprotein. The second fusion protein can comprise an immunoglobulin heavy chain polypeptide coupled to a second glycoprotein. The first and second fusion proteins associate to form heterodimer that further associate to form a tetramer comprising two heterodimeric complexes.

In certain aspects, glycoprotein peptide segments can be derived from HCV, i.e., HCV E1 and E2 glycoproteins. The immunoglobulin polypeptide segments can be derived from polypeptides that comprise the constant regions of antibodies. Conventional antibodies are large multi-subunit protein molecules comprising at least four polypeptide chains. For example, human IgG has two heavy chains (denoted by a subscript H) and two light chains (denoted by a subscript L) that are disulfide bonded to form the functional antibody. The size of a conventional IgG is about 150 kD. The heavy and light polypeptide chains of antibodies comprise variable (V) regions that directly participate in antigen interactions, and constant (C) regions that provide structural support and function in non-antigen-specific interactions with immune effectors. In vivo, a diverse primary repertoire of V genes that encode the $V_H$ and $V_L$ domains is produced by the combinatorial rearrangement of gene segments. C regions include the light chain C regions (referred to as $C_L$ regions) and the heavy chain C regions (referred to as $C_H$, or $CH_1$, $CH_2$ and $CH_3$ regions).

Members of the Flaviviridae family include the tick-borne viruses Hepatitis C virus, Gadgets Gully virus (GGYV), Kadam virus (KADV), Kyasanur Forest disease virus (KFDV), Langat virus (LGTV), Omsk hemorrhagic fever virus (OHFV), Powassan virus (POWV), Royal Farm virus (RFV), Tick-borne encephalitis virus (TBEV), and Louping ill virus (LIV).

The Togaviridae family includes Rubella virus, Sindbis virus, Eastern equine encephalitis virus, Western equine encephalitis virus, Venezuelan equine encephalitis virus, Ross River virus, and O'nyong'nyong virus.

The Herpesviridae family includes Herpes simplex virus-1 (HSV-1), Herpes simplex virus-2 (HSV-2), Varicella zoster virus (VZV), Epstein-Barr virus (EBV), Cytomegalovirus (CMV), Roseolovirus, Herpes lymphotropic virus, Roseolovirus, Kaposi's sarcoma-associated herpesvirus (KSHV) to name a few.

The Bunyaviridae family include Phlebovirus (Rift Valley Fever virus), Crimean-Congo hemorhagic virus, Nairovirus (Dugbe virus), Orthobunyavirus (Bunyamwere virus), and Hantavirus (Hantaan virus).

In certain aspects viral glycoproteins from a virus in these family of virus can be used in the context of the present invention.

B. Other Heterodimeric Glycoproteins

Heterodimeric glycoproteins include glycoprotein hormones, such as follicle-stimulating hormones (FSHs), luteinizing hormones (LHs), thyroid-stimulating hormones (TSHs), and chorionic gonadotropin (CG). These hormones, consisting of a common alpha subunit and a specific beta subunit, act through the FSH receptor (FSHR), the LH receptor (LHR), and the TSH receptor (TSHR) that are highly specific for their cognate hormones. These glycoprotein hormones are structurally and functionally conserved in various vertebrates.

In certain aspects heterodimeric glycoprotein hormones and other heterodimeric glycoproteins produced by animals can be used and produced in the context of the present invention.

C. Polypeptide Compositions

As used herein, a "protein" or "polypeptide" refers to a molecule comprising at least ten amino acid residues. In some embodiments, a wild-type version of a protein or polypeptide are employed, however, in many embodiments of the invention, a modified protein or polypeptide is employed to generate a therapeutic or an immune response. The terms described above may be used interchangeably. A "modified protein" or "modified polypeptide" refers to a protein or polypeptide whose chemical structure, particularly its amino acid sequence, is altered with respect to the wild-type protein or polypeptide. In some embodiments, a modified protein or polypeptide has at least one modified activity or function (recognizing that proteins or polypeptides may have multiple activities or functions). It is specifically contemplated that a modified protein or polypeptide may be altered with respect to one activity or function yet retain a wild-type activity or function in other respects, such as immunogenicity.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's GenBank and GenPept databases (on the World Wide Web at ncbi.nlm.nih.gov). The coding regions for these genes may be amplified and/or expressed using the techniques disclosed herein or as would be known to those of ordinary skill in the art.

Amino acid sequence variants of polypeptides of the invention can be substitutional, insertional, or deletion variants. A modification in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more non-contiguous or contiguous amino acids of the polypeptide, as compared to wild-type.

Deletion variants typically lack one or more residues of a parent, native, or wild-type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Figure 1:
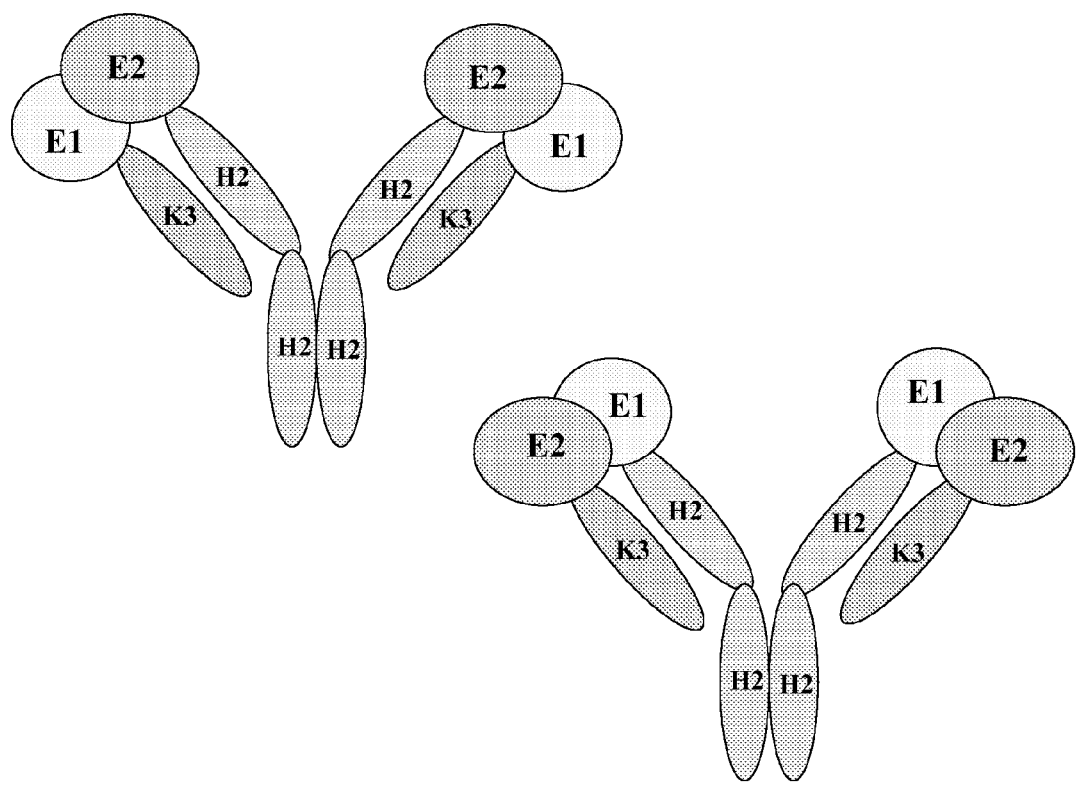
FIG. 1. Diagram of assembled IgG fusion protein with gpE1 and gpE2. Right: gpE1 is fused to the N-terminus of gamma chain (H2) and gpE2 to the N-terminus of k P19 were analyzed for HBc expression by polyclonal ELISA. Data are means+/−SD from four independently infiltrated samples.

Proteins of the invention may be recombinant. Alternatively, a non-recombinant or recombinant protein may be isolated from a plant. It is also contemplated that a plant containing such a variant may be used in compositions and methods of the invention. Consequently, a protein need not be isolated.

The term "functionally equivalent codon" is used herein to refer to codons that encode the same amino acid, such as the six codons for arginine or serine, and also refers to codons that encode biologically equivalent amino acids.

| Amino Acids | Codons |
|---|---|
| Alanine | Ala A GCA GCC GCG GCU |
| Cysteine | Cys C UGC UGU |
| Aspartic acid | Asp D GAC GAU |
| Glutamic acid | Glu E GAA GAG |
| Phenylalanine | Phe F UUC UUU |
| Glycine | Gly G GGA GGC GGG GGU |
| Histidine | His H CAC CAU |
| Isoleucine | Ile I AUA AUC AUU |
| Lysine | Lys K AAA AAG |
| Leucine | Leu L UUA UUG CUA CUC CUG CUU |
| Methionine | Met M AUG |
| Asparagine | Asn N AAC AAU |
| Proline | Pro P CCA CCC CCG CCU |
| Glutamine | Gln Q CAA CAG |
| Arginine | Arg R AGA AGG CGA CGC CGG CGU |
| Serine | Ser S AGC AGU UCA UCC UCG UCU |
| Threonine | Thr T ACA ACC ACG ACU |
| Valine | Val V GUA GUC GUG GUU |
| Tryptophan | Trp W UGG |
| Tyrosine | Tyr Y UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region. In certain aspects, polypeptides of the invention can incorporate amino acid linkers (e.g., $G_3SG_4S$ linker [SEQ ID NO: 37]), ER retention signals (e.g., KDEL retention signal [SEQ ID NO: 38]), and/or signal peptides (e.g., signal peptide of tissue plasminogen activator).

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity. In certain aspects the underlying DNA can be optimized for expression in plants without significantly altering the amino acid sequence of a polypeptide.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions of the invention, there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an HCV fusion protein.

The present invention contemplates the administration of HCV polypeptides or peptides to effect a preventative therapy against the development of a disease or condition associated with infection by a HCV.

The present invention also discloses combinations of HCV antigens that when combined lead to the production of an immunogenic composition that is effective at treating or preventing HCV infection. The effectiveness of the immune response can be measured either in animal model assays and/or using an opsonophagocytic assay.

In addition, U.S. Pat. No. 4,554,101 (Hopp), which is incorporated herein by reference, teaches the identification and preparation of epitopes from primary amino acid sequences on the basis of hydrophilicity.

D. Polypeptides and Polypeptide Production

The present invention describes polypeptides, peptides, proteins, and immunogenic fragments thereof for use in various embodiments of the present invention. In certain aspects, all or part of the proteins of the invention can be produced by recombinant DNA technology wherein a nucleotide sequence which encodes a peptide of the invention is inserted into an expression vector, transformed or transfected into an appropriate host cell and cultivated under conditions suitable for expression. In certain aspects, the expression vector can be a single vector encoding the first and the second glycoprotein (See below for a more detailed description of a single vector system).

One embodiment of the invention includes the use of gene transfer to cells, including plants and plant cells, for the production of proteins. The gene for the protein of interest may be transferred into appropriate host cells followed by culture or growth of cells under the appropriate conditions. The generation of recombinant expression vectors, and the elements included therein, are known to those of skill in the art and are generally discussed herein.

Polypeptides of the invention can be produced in transgenic plants (e.g., tobacco, maize, soybean and alfalfa). Plant expression vectors (see for example Hendy et al., 1999) and purification strategies coupled with an increase in transformable crop species render such methods a practical and efficient means of producing recombinant immunoglobulins not only for human and animal therapy, but for industrial applications as well (e.g., catalytic antibodies). Moreover, plant produced antibodies have been shown to be safe and effective and avoid the use of animal-derived materials and therefore the risk of contamination with a transmissible spongiform encephalopathy (TSE) agent. Further, the differences in glycosylation patterns of plant and mammalian cell-produced antibodies have little or no effect on antigen binding or specificity. In addition, no evidence of toxicity or HAMA has been observed in patients receiving topical oral application of a plant-derived secretory dimeric IgA antibody (see, e.g., Larrick et al., 1998.

Various methods may be used to express recombinant antibodies in transgenic plants. For example, antibody heavy and light chains can be independently cloned into expression vectors (e.g., *Agrobacterium tumefaciens* vectors), followed by the transformation of plant tissue in vitro with the recombinant bacterium or direct transformation using, e.g., particles coated with the vector which are then physically introduced into the plant tissue using, e.g., ballistics. Subsequently, whole plants expressing individual chains are reconstituted followed by their sexual cross, ultimately resulting in the production of a fully assembled and functional antibody. Similar protocols have been used to express functional antibodies in tobacco plants (see, e.g., Hiatt et al., 1989). In various embodiments, signal sequences may be utilized to promote the expression, binding and folding of unassembled antibody chains by directing the chains to the appropriate plant environment (e.g., the aqueous environment of the apoplasm or other specific plant tissues including tubers, fruit or seed) (see Fiedler et al., 1995). Plant bioreactors can also be used to increase antibody yield and to significantly reduce costs.

Additionally, animal cells can be used to produce polypeptides of the invention. Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth). Non-anchorage dependent or suspension cultures from continuous established cell lines are the most widely used means of large scale production of cells and cell products. However, suspension cultured cells have limitations, such as tumorigenic potential and lower protein production than adherent cells.

The protein or protein complex can be incorporated into an immunogenic composition of the invention. Immunogenic compositions of the invention comprise fusion proteins composed of HCV proteins, or immunogenic fragments of HCV proteins. In certain aspects, the immunogenic compositions comprise 2, 3, 4, or more HCV proteins and/or multiples of the same protein or protein fragment, or immunogenic fragments thereof in the same protein. In further aspects, the immunogenic composition will comprise two or more HCV E1 glycoproteins or segments thereof, and/or two or more HCV E2 glycoproteins or segments thereof In still further aspects fusion proteins can comprise heterologous sequences such as immunoglobulin domains or segments and/or purification tags (FLAG tag, myc tag, poly histidine, or viral surface proteins such as influenza virus haemagglutinin).

II. Nucleic Acids

In certain embodiments, the present invention concerns recombinant polynucleotides encoding the proteins, polypeptides, or peptides of the invention. The nucleic acid sequences of the HCV genome and nucleic acids encoding immunoglobulin domains and segments thereof can be used to prepare fusion proteins, polypeptide complexes, expression cassette and the like.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs of a polypeptide of the invention. It also is contemplated that a particular polypeptide may be encoded by nucleic acids containing variations having slightly different nucleic acid sequences but, nonetheless, encode the same or substantially similar protein.

In particular embodiments, the invention concerns isolated nucleic acid segments and recombinant vectors incorporating nucleic acid sequences that encode an HCV E1 glycoprotein, HCV E2 glycoprotein, immunoglobulin constant regions, segments of an immunoglobulin light chain, and/or a segments of immunoglobulin heavy chain. The term "recombinant" may be used in conjunction with a polypeptide and generally refers to a polypeptide produced from a nucleic acid molecule that has been manipulated in vitro or that is a replication product of such a molecule.

In other embodiments, the invention concerns isolated nucleic acid segments and recombinant vectors incorporating nucleic acid sequences that encode an HCV E1 glycoprotein, HCV E2 glycoprotein, immunoglobulin constant regions, segment of an immunoglobulin light chain, and/or a segment of immunoglobulin heavy chain that can induce an anti-HCV immune response in a subject.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length that can be used in recombinant nucleic acid protocols. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

The nucleic acid used in the present invention encodes HCV antigens, such as HCV glycoprotein E1 and/or HCV glycoprotein E2, including segments thereof. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein.

In certain other embodiments, the invention concerns isolated nucleic acid segments and recombinant vectors that include within their sequence a contiguous nucleic acid sequence or segment from SEQ ID NO:1 (HCV E1), SEQ ID NO:3 (HCV E2), SEQ ID NO:5, SEQ ID NO:7.

In certain embodiments, the present invention provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this invention using the methods described herein (e.g., BLAST analysis using standard parameters). In certain aspects, the isolated polynucleotide of the invention will comprise a nucleotide sequence encoding a polypeptide that has at least 80%, 85%, 90%, 95%, 96%, or 100% identity to an amino acid sequence of the invention, over the entire length of the sequence or over a particular segment of the polypeptide.

A. Plants for Producing Pharmaceuticals

The use of plants to produce important pharmaceutical proteins, including vaccine antigens and therapeutic monoclonal antibodies (mAbs), is attractive for several reasons. First, plants can produce large volumes of proteins efficiently and sustainably and, under certain conditions, can have significant advantages in manufacturing costs (Giddings 2001; Hood et al. 2002). Second, the growth of plants does not require animal- or human-derived nutrients and therefore has minimal risks of contamination with animal or human pathogens and toxins. Third, plants possess an endomembrane system and secretory pathway that are similar to mammalian cells (Vitale and Pedrazzini 2005), permitting appropriate post-translational modification of recombinant proteins, which are often critical to their proper functions.

Since the first demonstration of mAb expression in transgenic plants in 1989 (Hiatt et al. 1989), many different forms of mAbs have been produced in plant systems (reviewed in (Chen 2008; Ma 2003; Ma et al. 2005; Stoger et al. 2004)) using either transient, viral based expression systems (Canizares et al. 2005; Yusibov et al. 2006) or stably transgenic plants (Floss et al. 2007; Giddings et al. 2000; Twyman et al. 2005). The latter strategy suffers the long time frame required to generate transgenic plants and the generally low protein yields (<40 µg/g of fresh biomass). In contrast, plant viral vectors have the potential to rapidly produce high-levels of foreign proteins owing to their efficient replication and the resulting high copy numbers of gene of interest (Lico et al. 2008). However, until recently it has been difficult to efficiently express multi-component mAbs with plant viral vectors, because co-delivery of viral vectors built on the same virus backbone always results in early segregation and subsequent preferential amplification of one of the vectors in one cell—a common scenario of "competing replicons" (Dietrich and Maiss 2003; Diveki et al. 2002; Hull and Plaskitt 1970). This problem has been recently overcome by utilizing two sets of vectors derived from non-competing tobacco mosaic virus (TMV) and potato virus X (PVX), respectively, to produce full-size IgG at levels as high as 0.5 mg of mAb per gram leaf fresh weight (Giritch et al. 2006).

A bean yellow dwarf virus (BeYDV)-derived, three-component DNA replicon system has been developed that allows rapid high-yield production of single recombinant proteins in plants (Huang et al. 2009). This three component replicon system permits simultaneous efficient replication of two separate DNA replicons and high-level accumulation of two proteins encoded by the replicons. Moreover, a single vector was constructed that contains multiple replicon cassettes that was as efficient as the three-component system in directing expression of two distinct protein molecules. Using either the non-competing, three-vector system or the multi-replicon single vector, both the heavy and light chain molecules of a protective IgG mAb 6D8 against Ebola virus GP1 were produced (Wilson et al. 2000) at ~0.5 mg of mAb per gram leaf fresh weight (LFW) within 4 to 8 days post infiltration (dpi) of *Nicotiana benthamiana* leaves. The full-size IgG complex containing two heavy chains and two light chains was efficiently assembled, readily purified, and functioned properly to bind inactivated Ebola virus. Thus, the single-vector replicon system provides high-yield production capacity, eliminates the difficult task of identifying non-competing virus, and obviates the need for co-infection of multiple expression modules. The multi-replicon vector represents a significant advance in transient expression technology for antibody production in plants.

B. Vectors

Polypeptides of the invention may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Useful vectors encoding such fusion proteins include BeYDV-derived vector (Huang et al. 2009; Wilson et al. 2000), pIN vectors (Inouye et al., 1985), vectors encoding a stretch of histidines, and pGEX vectors, for use in generating glutathione S-transferase (GST) soluble fusion proteins for later purification and separation or cleavage.

Vectors of the invention may be used in a host cell to produce polypeptides of the invention. The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

In certain aspects, the invention is directed to a single vector system that comprises a polynucleotide having a first and second nucleic acid segment encoding a first and second glycoprotein. The first nucleic acid segment comprising a first promoter and a region encoding a first product of interest (e.g., a glycoprotein), the first coding segment being flanked on either side by at least a portion of a long intergenic region (LIR) of a geminivirus genome. The second nucleic acid segment comprising a second promoter and a region encoding a second product of interest (e.g., a second glycoprotein), the second coding segment being flanked on either side by at least a portion of a long intergenic region (LIR) of a geminivirus genome. The single vector system having a third nucleic acid segment comprising a third promoter and a nucleic acid encoding a Rep/RepA protein of a geminivirus genome. As used herein, the long intergenic region (LIR) contains a rep binding site capable of mediating excision and replication by a geminivirus Rep protein. In some embodiments, the first and/or the second nucleic acid segment may further comprise a short intergenic region (SIR) of a geminivirus genome. A short intergenic region (SIR) of a geminivirus genome refers to the complementary strand (the short IR (SIR) of Mastreviruses). The nucleic acid segment comprising the products of interest may be any length that can be incorporated into the replicon.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Where a plant cell is targeted, it is preferable to position the polynucleotide coding region adjacent to and under the control of a promoter that is capable of being expressed in a plant cell. Generally speaking, such a promoter might include either a bacterial, plant, human or viral promoter.

2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments, the use of internal ribosome entry sites (IRES) elements are used to create multigene or polycistronic messages. IRES elements are able to bypass the ribosome scanning model of 5' methylated cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Selectable and Screenable Markers

In certain embodiments of the invention, cells containing a nucleic acid construct of the present invention may be identified by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

C. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, plant cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (accessible on the world wide web at atcc.org). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe,* and *Pichia pastoris.*

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

D. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

E. Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium mediated transformation (U.S. Pat. Nos. 5,591,616 and 5,563,055, each incorporated herein by reference); or by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985). Through the application of techniques such as these, organelle(s), cell(s), tissue(s) or organism(s) may be stably or transiently transformed.

III. Pharmaceutical Compositions and Administration

The present invention includes methods for preventing or ameliorating HCV infections. As such, the invention contemplates vaccines and therapeutic compositions for use in both active and passive immunization embodiments. Immunogenic compositions, proposed to be suitable for use as a vaccine or therapeutic, may be prepared from immunogenic HCV polypeptide(s), such as an HCV E1 or E2 antigen or immunogenic fragments thereof. In certain aspects the antigenic material is dialyzed to remove undesired small molecular weight molecules and/or lyophilized for more ready formulation into a desired vehicle.

The preparation of vaccines or therapeutics that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such compositions are prepared as injectables either as liquid solutions or suspensions: solid forms suitable for solution in or suspension in liquid prior to injection may also be prepared. The preparation may also be emulsified. The active ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

Polypeptides and polypeptide-encoding DNA constructs may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Typically, vaccines are administered in a manner compatible with the dosage formulation, and in such amount as will be therapeutically effective and/or immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms active ingredient per vaccination or administration. Suitable regimes for initial administration and booster shots are also variable, but are typified by an initial administration followed by subsequent inoculations or other administrations.

The manner of application may be varied widely. Any of the conventional methods for administration of a vaccine or therapeutic are applicable. These are believed to include oral application on a solid physiologically acceptable base or in a physiologically acceptable dispersion, parenterally, by injection and the like. The dosage of the vaccine or therapeutic will depend on the route of administration and will vary according to the size and health of the subject.

In certain instances, it will be desirable to have multiple administrations of the vaccine or therapeutic, e.g., 2, 3, 4, 5, 6 or more administrations. Administrations can be at 1, 2, 3, 4, 5, 6, 7, 8, to 5, 6, 7, 8, 9, 10, 11, 12 twelve week intervals, including all ranges there between. Periodic boosters at intervals of 1-5 years will be desirable to maintain protective levels of the antibodies or therapeutic effect. The course of the immunization may be followed by assays for antibodies against the antigens, as described in U.S. Pat. Nos. 3,791,932; 4,174,384 and 3,949,064.

The immunogenicity of polypeptide or peptide compositions can be enhanced by the use of non-specific stimulators of the immune response, known as adjuvants. Suitable adjuvants include all acceptable immunostimulatory compounds, such as cytokines, toxins, or synthetic compositions. A number of adjuvants can be used to enhance an antibody response against an HCV polypeptide. Adjuvants can (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum salts, such as aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion. Others adjuvants or methods are exemplified in U.S. Pat. Nos. 6,814,971, 5,084,269, 6,656,462, each of which is incorporated herein by reference).

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide monooleate (Aracel A)); or emulsion with a 20% solution of a perfluorocarbon (Fluosol-DA®) used as a block substitute may also be employed to produce an adjuvant effect. Examples of adjuvants include complete Freund's adjuvant (a non-specific stimulator of the immune response containing killed *Mycobacterium tuberculosis*), incomplete Freund's adjuvants, and aluminum hydroxide.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-12 or genes encoding proteins involved in immune helper functions, such as B-7.

A. Lipid Components and Moieties

In certain embodiments, the present invention concerns compositions comprising one or more lipids associated with a nucleic acid or a polypeptide/peptide. A lipid is a substance that is insoluble in water and extractable with an organic solvent. Compounds other than those specifically described herein are understood by one of skill in the art as lipids, and are encompassed by the compositions and methods of the present invention. A lipid component and a non-lipid may be attached to one another, either covalently or non-covalently.

A lipid may be a naturally occurring lipid or a synthetic lipid. However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or a polypeptide/peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid composition of the present invention is not limited to any particular structure. For example, polypeptide compositions or nucleic acids may also be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL) or Superfect (Qiagen) complex is also contemplated.

In certain embodiments, a composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or any range there between, of a particular lipid, lipid type, or non-lipid component such as an adjuvant, antigen, peptide, polypeptide, sugar, nucleic acid or other material disclosed herein or as would be known to one of skill in the art. In a non-limiting example, a composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a non-lipid component. Thus, it is contemplated that compositions of the present invention may comprise any of the lipids, lipid types or other components in any combination or percentage range.

B. Combination Therapy

The compositions and related methods of the present invention may also be used in combination with the administration of traditional therapies. These include, but are not limited to, the administration of anti-viral therapies (interferon α, ribavirin, or the like) and/or liver transplant.

In one aspect, it is contemplated that a polypeptide vaccine and/or therapy is used in conjunction with antiviral treatment. Alternatively, the therapy may precede or follow the other agent or treatment by intervals ranging from minutes to weeks. In embodiments where the other agents and/or a proteins or polynucleotides are administered separately, one would generally ensure that a significant period of time did not expire between the time of each delivery or treatment, such that the treatment, agent, and/or composition described herein would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations may be employed, for example antiviral therapy is "A" and the immunogenic or therapeutic composition described herein, is "B":

| | | | | | | |
|---|---|---|---|---|---|---|
| A/B/A | B/A/B | B/B/A | A/A/B | A/B/B | B/A/A | A/B/B/B B/A/B/B |
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | |

Administration of the immunogenic compositions of the present invention to a patient/subject will follow general protocols for the administration of such compounds, taking into account the toxicity, if any, of the HCV composition. It is expected that the treatment cycles would be repeated as necessary. It also is contemplated that various standard therapies, such as hydration, may be applied in combination with the described therapy.

C. General Pharmaceutical Compositions

In some embodiments, pharmaceutical compositions are administered to a subject. Different aspects of the present invention involve administering an effective amount of a composition to a subject. In some embodiments of the present invention HCV polypeptides may be administered to the patient to protect against HCV infection or to treat HCV infection. Additionally, such compounds can be administered in combination with an antiviral. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including creams, lotions, mouthwashes, inhalants and the like.

The active compounds of the present invention can be foil iulated for parenteral administration, e.g., formulated for injection via the intravenous, intramuscular, sub-cutaneous, or even intraperitoneal routes. Typically, compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients. For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

D. Antibodies and Passive Immunization

Another aspect of the invention is a method of preparing an immune globulin for use in prevention or treatment of HCV infection comprising the steps of immunizing a recipient with the vaccine of the invention and isolating immune globulin from the recipient. An immune globulin prepared by this method is a further aspect of the invention. A pharmaceutical composition comprising the immune globulin of the invention and a pharmaceutically acceptable carrier is a further aspect of the invention which could be used in the manufacture of a medicament for the treatment or prevention of HCV infection. A method for treatment or prevention of HCV infection comprising a step of administering to a patient an effective amount of the pharmaceutical preparation described herein is a further aspect of the invention.

Inocula for polyclonal antibody production are typically prepared by dispersing the immunogenic composition in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies. The antibodies can be isolated to the extent desired by well known techniques such as affinity chromatography (Harlow and Lane, 1988). Antibodies can include antiserum preparations from a variety of commonly used animals, e.g., goats, primates, donkeys, swine, horses, guinea pigs, rats or man. The animals are bled and serum recovered.

An immune globulin produced in accordance with the present invention can include whole antibodies, antibody fragments or subfragments. Antibodies can be whole immunoglobulins of any class e.g. IgG, IgM, IgA, IgD or IgE, chimeric antibodies or hybrid antibodies with dual specificity to two or more antigens of the invention. They may also be fragments, e.g., F(ab')2, Fab', Fab, Fv and the like including hybrid fragments. An immune globulin also includes natural, synthetic or genetically engineered proteins that act like an antibody by binding to specific antigens to form a complex.

A vaccine or therapeutic composition of the present invention can be administered to a recipient who then acts as a source of immune globulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat HCV infection. Hyperimmune globulins of the invention are particularly useful for treatment or prevention of HCV in infants, immune compromised individuals or where treatment is required and there is no time for the individual to produce antibodies in response to vaccination.

IV. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

EXAMPLE 1

Protein Production in Plants

I. Results

The three-vector BeYDV replicon system is non-competing. It was previously shown (Huang et al., 2009) that a BeYDV-derived three-vector (e.g., pBYGFP, pREP110 and pP19) transient expression system provides extremely efficient replication of a single DNA replicon and high-level expression in plant cells of protein encoded by the single replicon vector (e.g., pBYGFP). In studying whether two replicon vectors encoding different proteins can be co-expressed, N. benthamiana leaves were infiltrated with BYGFP and/or BYDsRed in combination with REP110 and P19 vectors. BYGFP/REP110/P19 and BYDsRed/REP110/P19 infiltrated areas displayed green and red fluorescence, respectively, while the fluorescence of BYGFP/BYDsRed co-infiltrated area appeared yellow, probably due to overlapping of both green and red fluorescence. Mesophyll protoplasts were subsequently isolated from infiltrated areas and observed under fluorescence microscope. When two populations of protoplasts that individually expressed BYGFP or BYDsRed were mixed, no overlapping fluorescent protoplast was observed. In contrast, the majority (>80%) of the fluorescent protoplasts from co-infiltration of BYGFP/BYDsRed exhibited both green and red fluorescence, indicating the efficient co-expression of GFP and DsRed in the same cells.

To determine whether amplification of both replicons is efficient, Southern blot of DNA extracted from co-infiltrated leaves was performed. An ethidium bromide-stained gel showed the expected ~3 kbp band in the BYGFP/REP110/P19, the BYDsRed/REP110/P19, and the BYGFP/BYDsRed/REP110/P19 samples, indicating efficient formation of DNA replicons. No discrete bands were observed in DNA samples from uninfiltrated, BYGFP alone, or BYDsRed alone leaves. Southern blotting with both GFP and DsRed probes showed that the BYGFP/REP110/P19 replicon reacted with only the GFP probe, while the BYDsRed/REP110/P19 bound only the DsRed probe. However, the BYGFP/BYDsRed/REP110/P19 sample produced positive signals for both GFP and DsRed probes, with the signal intensity similar to those representing the corresponding single replicons, suggesting that the BYGFP and BYDsRed replicons are near-equally co-expressed. Together, these results demonstrate that the BeYDV replicon system is non-competing, which enables its application in producing multiple-subunit proteins of pharmaceutical importance, such as mAbs.

High-yield transient expression of a protective mAb against Ebola virus using non-competing replicon vectors. A protective mAb against Ebola virus glycoprotein GP1 (6D8) was expressed (Huang et al., 2010) by co-infiltration of N. benthamiana leaves with two replicon vectors, pBY-H(6D8) and pBY-L(6D8), encoding the heavy chain and light chain subunits of 6D8 mAb, respectively, along with vectors for REP110 and P19. ELISA showed that 6D8 mAb accumulated within 2 dpi and rapidly reached a peak in 4 dpi at 0.4-0.5 mg/g LFW. Western blot with SDS-PAGE under reducing condition confirmed the presence of both light and heavy chains with the expected molecular weights of 25 kDa and 50 kDa, respectively. When the same samples were analyzed under non-reducing condition, a ~170 kDa band was observed, which represents the fully assembled heterotetrameric form of 6D8 mAb. The slightly higher molecular weight (~170 kDa vs. the calculated 150 kDa) suggests that 6D8 is glycosylated as predicted for proteins with potential N-link glycosylation sites targeted to the endomembrane system of plant cells. The western blots also indicated that no proteolytic clipping of the light or heavy chains occurred, since only the expected size bands were observed.

Two replicons can be delivered in a single vector. A single vector replicon containing a native REP expression cassette (C1/C2 coding region under the control of the viral LIR promoter, e.g., pBYGFP.R) works as well as the three-vector system for the expression of GFP (Huang et al., 2009). To test if the single-vector replicon system can be used to simultaneously express multiple proteins, the inventors constructed pBYGFPDsRed.R for co-expression of GFP and DsRed (Huang et al., 2010). Examination of protoplasts prepared from pBYGFPDsRed.R infiltrated leaves showed that both GFP and DsRed fluorescence were simultaneously detected in ~95% of the fluorescent protoplasts, indicating high-efficiency co-expression of both fluorescent proteins within same cells. Analyses of DNA from infiltrated leaves reveals the BYGFPDsRed.R sample produced replicons of different sizes which also reacted differently with GFP or DsRed probes, indicating the simultaneous presence of GFP and DsRed replicons. For the BYGFPDsRed.R sample, the strongest DsRed-probe-reacting band is ~3.5 kb, which is similar to the size of the BYGFP.R replicon, suggesting this band represents the DsRed replicon comprising the 35S/TEV 5'-DsRed-VSP 3'-SIR-C2/C1 sequence within the two LIRs; while the top GFP-probe-reacting band is ~2.6 kb, which is expected for a smaller replicon consisting of the 35S/TMV 5'-GFP-rbcS 3'-SIR region between two adjacent LIR elements. These results demonstrate that the two tandemly linked replicons can be released and amplified independently, leading to high-level proliferation of two distinct double-stranded DNA replicons and efficient expression of both proteins. It was also observed that in the BYGFPDsRed.R lanes a ~1.6 kb band reacted with the GFP probe and a slightly higher ~1.7 kb band less strongly with the DsRed probe, representing the single-strand DNA forms of the corresponding replicons. Overall, the data indicate that the multi-replicon single vector system produces high-level co-expression of two target proteins.

Co-expression and assembly of full-size IgG by the multi-replicon single vector. To further demonstrate the effectiveness of the multi-replicon single-vector system, pBY-HL(6D8).R was used, which harbors expression cassettes for the light and heavy chains of 6D8 mAb and REP (C1/C2) (Huang et al., 2010). ELISA of pBY-HL(6D8).R leaf extracts showed that 6D8 mAb accumulated to a level comparable to that produced by the co-infiltration of four separate vectors. The time course of the expression of 6D8 mAb with this single vector was also similar to that obtained with separate vectors. Furthermore, SDS-PAGE and western blot analyses demonstrate that the mAb produced by pBY-HL(6D8).R has the correct light and heavy chain components and is fully assembled.

Purification and characterization of the replicon-expressed full-size IgG antibody. To further validate the multi-replicon single-vector expression system and to examine the structural and functional properties of the plant-made IgG, ammonium sulfate precipitation followed by protein G affinity chromatography was used to purify the single-vector-derived 6D8 mAb (Huang et al., 2010). SDS-PAGE Coomassie blue staining analysis of purification fractions showed that 35% ammonium sulfate effectively removed the most abundant plant host protein RuBisCo, and other plant proteins. Protein G affinity chromatography removed other contaminating proteins and 6D8 mAb was purified to >90% purity with intact light and heavy chains. A similar analysis under non-reducing condition indicated that the purified 6D8 antibody is in its fully assembled tetrameric form. The purified mAb was further examined in a binding assay in which different concentrations of plant-derived 6D8 were incubated with irradiated Ebola virus. A generic human IgG was used as a negative control for the assay. The $OD_{450}$ increased as more 6D8 mAb was applied in the reaction. In contrast, the $OD_{450}$ for a generic human IgG remained at a basal level regardless the amount of this IgG used for the reaction. This result indicates that plant produced 6D8 retains its specific affinity for Ebola virus GP1 protein. Analyses for 6D8 produced by co-infiltration of plant leaves with separate light chain and heavy chain replicons showed similar results in antibody purity, SDS-PAGE pattern, and its ability to specifically bind to Ebola virus.

II. Methods

Vector construction. The construction of plasmids pREP110, pP19, pBYGFP and pBYGFP.R has been previously described (Huang et al., 2009).

For the construction of pBYDsRed, the DsRed gene was amplified from pDsRed1-1 (Clontech cat #6922-1) with primers 5'-ATCGTCTAGAACCATGGTGCGCTCCTC-CAAG (SEQ ID NO:14) and 5'-ATTAGAGCTCCTACAG-GAACAGGTGGTG (SEQ ID NO:15), digested with XbaI and SacI, and ligated into pIBT210 to make pIBT-DsRed, from which the XhoI-SacI fragment was substituted into pBYGFP to make pBYDsRed. Tandem dual replicon constructs used CaMV 35S promoters with a single enhancer element, obtained by amplification of the expression cassettes in pBYDsRed and pIBT210.3 (Judge et al., 2004) with primers 35S-Sda (5'-TGACCTGCAGGCATGGTGGAG-CACGACA (SEQ ID NO:16) and VSPHT (5'-TGAATAGT-GCATATCAGCATACCTTA (SEQ ID NO:17). The promoter and 5'-UTR of TMV in the fragment amplified from pIBT210.3, the GFP gene from pBYGFP, and the pea ribulose1,5-bisphosphate carboxylase small subunit (rbcS) terminator (Friedrichsen et al., 2000) were ligated together into the PstI and EcoRI sites of pBY024 (Mor et al., 2003) to make pBYGFP210.3. The fragment containing the GFP replicon, obtained by digestion of pBYGFP210.3 with BamHI, filling with Klenow enzyme, and then digestion with AscI, was ligated with the 35S-Sda amplified pBYD-sRed replicon digested with AscI, filled with Klenow enzyme, and then SacI, into the vector pBYHBc.R (Huang et al., 2009) that had been digested with AscI and SacI, to make pBY-GFPDsRed.R.

The gene sequences for heavy (H2) and light (K3) chains of mouse monoclonal antibody 6D8 (Wilson et al., 2000) were de-immunized for humans by substitution of human constant region sequences for gamma type 1 and kappa chains (Biovation, Edinburgh, Scotland). The resulting sequences were used to design plant codon-optimized genes, and synthesized commercially (Retrogen, San Diego, CA). The H2 gene in pCHF4-6D8-H2 (Mapp Biopharmaceutical, Inc.) was end-tailored to add a C-terminal 'SEKDEL' (SEQ ID NO: 39) hexapeptide by PCR with the primer H2-SEKDEL-Kpn (5'-GCGGTACCTTAAAGCTCATCCT-TCTCTGATTTACCCGGAGACAAGGAGAG (SEQ ID NO: 18), digested with NcoI and KpnI, and inserted into pPS1 (Huang and Mason, 2004) to make p6D8-H2, from which the XhoI-EcoRI fragment containing TEV5'-UTR-H2-VSP3' was substituted into pBYGFP to make pBYH (6D8). The K3 gene in pCHF4-6D8-K3 (Mapp Biopharmaceutical, Inc.) was obtained as an NcoI-KpnI fragment, ligated with the 35S promoter-TMV5' and the rbcS3' elements, and substituted into pBYGFP vector to make pBY-L(6D8). The replicon (LIR to SIR) from pBY-L(6D8) was substituted into pBYGFP.R to make pBYK3R. The H2-SEKDEL (SEQ ID NO: 39) fragment was amplified from pBY-H(6D8) with primers H2-Xba (5'- ACGATCTA-GAACAATGGGATGGTCTTGCATC (SEQ ID NO:19)) and VSPHT, digested with XbaI and KpnI, and substituted into the vector pBY027 (Mor et al., 2003) to make pBY-H2K210. The replicon from pBY-H2K210 was then inserted into pBYK3R to make the tandem dual replicon construct pBY-HL(6D8).R.

Agroinfiltration of Nicotiana benthamiana leaves. Binary vectors were separately introduced into Agrobacterium tumefaciens LBA4404 by electroporation. The agroinfiltration procedure was performed as previously described (Huang et al., 2009).

Plant DNA extraction and Southern blotting. Total DNA extraction and Southern blotting was performed as previously described (Huang et al., 2009). Digoxygenin (DIG)-labeled gene-specific probes were synthesized by PCR with primers (5'-GTCACCATGGTGAGCAAGGGCGAG (SEQ ID NO:20)) and (5'-CTCAGGATCCTTACTTGTACA-GCTCGTC (SEQ ID NO:21) for the GFP gene, and with primers (5'-ATCGTCTAGAACCATGGTGCGCTCCTC-CAAG (SEQ ID NO:22) and (5'-ATTAGAGCTCCTACA-GGAACAGGTGGTG (SEQ ID NO:23) for the DsRed gene, respectively, according to the manufacturer's instructions (Roche Applied Science, Indianapolis, Ind.).

Plant tissue harvest. For expression time-course experiments, Agroinfiltrated Nicotiana benthamiana leaves were harvest on days 2, 4, 6, and 8 dpi. For other protein analysis, plant leaves were harvest 4 dpi.

Protein extraction. Total leaf protein was homogenized with extraction buffer (25 mM sodium phosphate, pH 6.6, 100 mM NaCl, 1 mM EDTA, 0.1% TritonX-100, 10 mg/ml sodium ascorbate, 10 µg/ml leupeptin, 0.3 mg/ml PMSF) using a FastPrep machine following the manufacture's instruction. The crude plant extract was clarified by centrifugation at 14,000 g for 10 min at 4° C.

ELISA. The clarified total protein extract was analyzed by ELISA designed to detect the assembled form of mAb (with both light and heavy chains) as described previously (Giritch et al., 2006). Briefly, plates were coated with a goat anti-human IgG specific to gamma heavy chain (Southern Biotech, AL). After incubation with plant protein extract, a HRP-conjugated anti-human-kappa chain antibody (Southern Biotech, AL) was used as the detection antibody, using human IgG reference standard (Southern Biotech, AL).

SDS-PAGE and western blot. SDS-PAGE and western blotting were performed as previously described (Santi et al., 2008). Briefly, plant protein example or human IgG standard was mixed with sample buffer either under reducing or non-reducing condition and then subjected to SDS-PAGE. PAGE gels were either stained with Coomassie blue or used to transfer proteins onto PVDF membranes. The anti-human gamma and kappa specific antibodies described above (ELISA) were used for western blot analysis.

Antigen binding assay. Polyvinyl chloride 96-well ELISA plates were coated with 50 µl of 1:1000-diluted irradiated Ebola virus (a gift from Dr. William Pratt, USAMRIID) and incubated at 4° C. for 12 hr. Plates were blocked with 5% skim milk in PBST (10.6 mM $Na_2HPO_4$, 2.9 mM $KH_2PO_4$, 104.7 mM NaCl, 0.05% Tween-20) at room temperature for 2 hrs. Subsequently, the plates were incubated with different concentrations of the plant-derived 6D8 mAb or human IgG (Southern Biotech, AL) diluted in 1% skim milk in PBST for 1 hr at 37° C. HRP-conjugated goat anti-human IgG (Southern Biotech) was then added and incubated for 1 hr at 37° C. The plates were developed with TMB substrate (KPL inc., MD) and the OD was read at 450 nm.

6D8 antibody purification. N. benthamiana leaves Infiltrated with 6D8 mAb constructs were harvest on 4 dpi and were homogenized with the extraction buffer (25 mM sodium phosphate, pH 6.6, 100 mM NaCl). Crude extract was filtered through Miracloth and centrifuged at 17,700 g for 15 min at 4° C. to remove cell debris. Ammonium sulfate was slowly added to the clarified plant extracts to 35% saturation with thorough mixing at 4° C. The sample was centrifuged at 17,700 g for 15 min at 4° C. and the pellet was saved for analysis. The 35% ammonium sulfate supernatant was further processed by adding ammonium sulfate to 60% saturation. The sample was again centrifuged at 17,700 g for 15 min and the supernatant was discarded. The 60% ammonium sulfate pellet was resuspended in the extraction buffer and was then applied to a Protein G column (Pierce, Ill.). After sample loading, the resin was washed with the extraction buffer and the column was eluted with 50 mM sodium citrate, pH 2.5. The elution fraction was neutralized immediately with 1M Tris-base to a final pH of 7.5.

Isolation of *N. benthamiana* mesophyll protoplasts and fluorescence microscopy. Protoplasts were released from infiltrated leaf tissue by incubation for 10-16 hours at room temperature in a solution containing 0.4 M mannitol, 8 mM $CaCl_2$, 0.4% cellulase and 0.4% Macerozyme R-10. Released protoplasts were filtrated through a nylon mesh with a 62-µm pore diameter.

Visualization of GFP and DsRed. Leaves co-expressing GFP and DsRed were viewed under a UVGL-25 lamp (UVP, Upland, Calif.). Protoplasts were viewed with a Nikon inverted microscope with GFP filter sets (Chroma #41028; excitation filter, 500/20 nm; emission filter, 535/30 nm) and DsRed filter sets (Chroma #42005; excitation filter, 540/40 nm; emission filter, 600/50 nm).

EXAMPLE 2

Production of gpE1/E2-IgG Fusion Proteins gpE1/E2-IgG fusion proteins (E1-kappa chain coexpressed with E2-gamma chain) have been expressed in and purified from leaves of *N. benthamiana*. The recombinant material assembles Ig-like complexes and can be readily purified by protein A affinity. The human IgG component will mediate targeting to dendritic cells for more efficient immunization in humans.

A single-vector replicon-based expression system has been developed for high-level rapid production of vaccine antigens in plants. Transient expression of NS345 replicon vectors in plant leaves has resulted in DNA replicon formation and NS345 polyprotein accumulation. A stable *N. benthamiana* lines transgenic with the NS345 replicon vector have been established.

Construction of IgG fusion proteins with gpE1 and gpE2. The expression and partial purification of HCV gpE1/gpE2 in *Nicotiana benthamiana* has been shown. The inventors created fusion proteins that allow assembly of gpE1/E2 complexes and at the same time allow efficient purification of the recombinant protein. It was reasoned that fusions with immunoglobulin G (IgG) heavy and light (H & L) chains would allow assembly to juxtapose the gpE1 and gpE2 moieties, and that protein A/G affinity could be applied for efficient purification. FIG. 1 shows a diagram of the structure of assembled gpE1-kappa (E1-K3) and gpE2-gamma (E2-H2) fusion proteins, with the gpE1 or gpE2 fused to the N-terminus of the Ig chains.

Kappa and gamma chains of a plant codon optimized monoclonal antibody 6D8, which binds to a linear epitope of Ebola virus glycoprotein, were used (Huang et al., 2010). The genes were available from a previous project to express the 6D8 mAb in plants described above. The plant-optimized gpE1 gene (codons 192-358 of HCV GenBank M62321) with N-terminal TPA signal peptide was fused via a linker $(G_4S)_2$ to the mature plant-optimized 6D8 kappa chain including variable region to make E1-K3. Specifically, a reverse primer containing the linker coding sequence and a BamHI site (E1-L-Bam: 5'-CCAGGATCCGCCACCTC-CTGATCCACCTCCGCCTGCAAGGACTCCCCA (SEQ ID NO:24)) was used with the forward primer omega-Xho (5'-TTGGCTCGAGTATTTTTACAACAATTACC (SEQ ID NO:25)) to amplify the E1 coding sequence from template pBYsE1b210.3, using a high-fidelity thermostable polymerase. The resulting product was digested with XhoI and BamHI. The coding sequence of the light chain (K3) of mAb 6D8 was PCR amplified from pBY-L(6D8) (Huang et al., 2010) using the forward primer to introduce a BamHI site (K3-Bam-F: 5'-GTCGGATCCGATGTTTTGATGACT-CAAAGC (SEQ ID NO:26)) and the reverse primer VSPHT (5'-TGAATAGTGCATATCAGCATACCTTA (SEQ ID NO:27)), and digested with BamHI and KpnI. The two digested PCR products were ligated together with pBluescriptKS (digested with XhoI and KpnI) to make pBlue-E1K3, which was verified by DNA sequencing. The entire E1-K3 fusion protein coding sequence was obtained from pBlue-E2H2 digested with XhoI and KpnI, and ligated with pBYR1/XhoI-KpnI to make pBYR-E1K3, which places the coding sequence under the control of the CaMV 35S promoter, within a bean yellow dwarf geminivirus replicon in a T-DNA vector for *Agrobacterium*-mediated DNA delivery to plant cells.

The plant optimized gpE2 gene (codons 384-708) was fused via linker $(G_4S)_2$ to the mature plant-optimized 6D8 gamma chain including its variable region to make E2-H2). Specifically, a reverse primer containing the linker coding sequence and a BamHI site (E2-708L-Bam: 5'-AACG-GATCCACCTCCACCTGATCCACCTCCACCACTT-GATCCCACACCGTAC (SEQ ID NO:28)) was used with the forward primer TEVHT (5'-CAAGCATTCTACTTCT-ATTGCAGC (SEQ ID NO:29)) to amplify the E2 coding sequence from the template pBYsE2T, using a high-fidelity thermostable polymerase. The resulting product was digested with XbaI and BamHI. The coding sequence of the heavy chain of mAb 6D8 was PCR amplified from pBY-H (6D8) (Huang et al., 2010) using the forward primer to introduce a BamHI site (H2-Bam-F: 5'-GTCGGATCCGAT-GTTCAGCTTCTTGAGTCTGGAG (SEQ ID NO:30)) and the reverse primer VSPHT (5'-TGAATAGTGCATATCAG-CATACCTTA (SEQ ID NO:31)), and digested with BamHI and SacI. The two digested PCR products were ligated together with pBluescriptKS (digested with XbaI and SacI) to make pBlue-E2H2, which was verified by DNA sequencing. The entire E2-H2 fusion protein coding sequence was obtained from pBlue-E2H2 digested with XbaI and SacI, and ligated with pBYR1/XbaI-SacI to make pBYR-E2H2, which places the coding sequence under the control of the CaMV 35S promoter, within a bean yellow dwarf geminivirus replicon in a T-DNA vector for *Agrobacterium*-mediated DNA delivery to plant cells.

The converse E1-H2 and E2-K3 fusions were also constructed in a similar fashion. These coding sequences were inserted into the geminiviral replicon vector pBYR1 to make pBYR-E1H2 and pBYR-E2K3. A dual replicon vector for co-expression of E2-H2 and E1-K3 fusion proteins was constructed using a 4-fragment ligation. pBY-HL(6D8).R (Huang et al., 2010) was digested with XbaI-KpnI and the larger vector fragment obtained. pBlue-E2H2 (described above) was digested with XbaI-HindIII to obtain a 1643 bp fragment. pBY-HL(6D8).R (Huang et al., 2010) was digested with HindIII-NcoI to obtain a 2552 bp fragment. pBlue-E1K3(described above) was digested with NcoI-KpnI to obtain a 1283 bp fragment. Ligation of the 4 fragments yielded pBYR-E2H-E1K, in which the two expression cassettes for E2-H2 and E1-K3 lie in separate geminiviral replicons linked in tandem.

Figure 2:
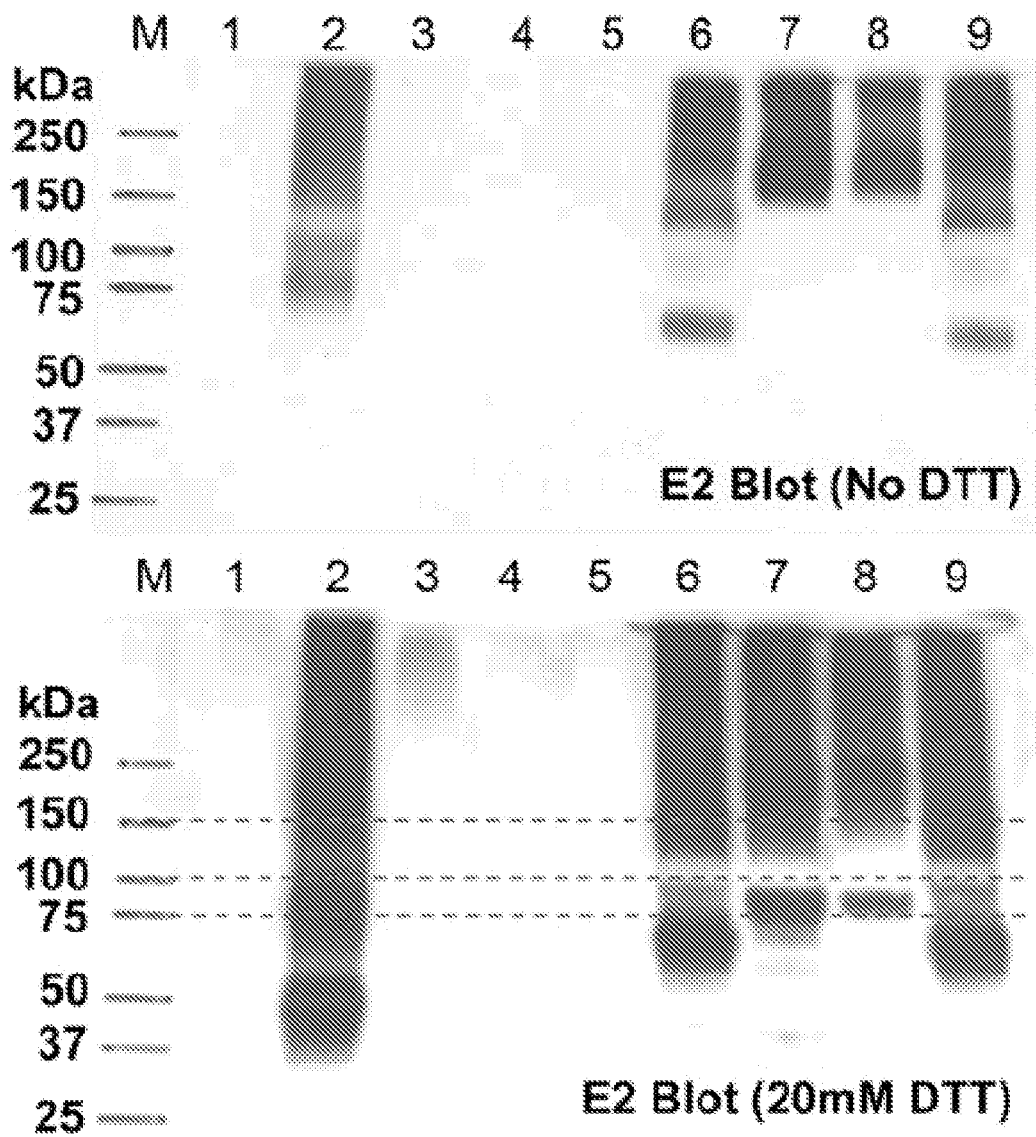

Expression of gpE1/E2-IgG fusion proteins. Fusion proteins were co-expressed in *N. benthamiana* leaf. Samples were examined by Western blot that was probed with a linear anti-E2 mAb under non-reducing conditions, which showed the E2-H2 fusion produced a strong band at ~150 kDa, suggesting a dimer of the heavy chain (FIG. 2, lane 7). Co-expression of E1-K3 and E2-H2 (lane 8) showed larger material indicating assembly of heavy and light chains. The converse E1-H2 and E2-K3 fusions co-expressed also indicated assembly, but produced smaller bands suggesting partial degradation (FIG. 2, lane 9).

Figure 3:
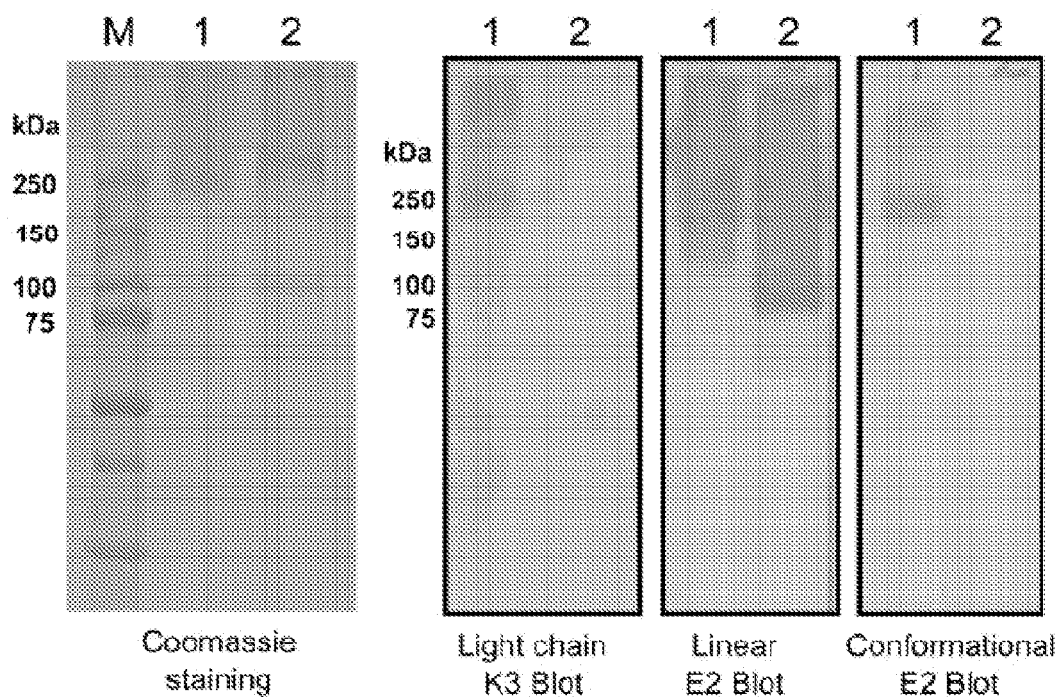

Purification of gpE1/E2-IgG fusion protein. The E1-K3+E2-H2 fusions were used in larger scale expression (20 plants, ~180 g leaves). Leaves were extracted in a blender with 500 ml of extraction buffer (20 mM Tris pH 7.5, 40 mM KCL, 1 mM EDTA, 0.3 mM PMSF), and obtained the ammonium sulfate precipitation (35-65%) fraction containing the fusion proteins. Protein A affinity was used to purify the IgG fraction. SDS-PAGE of the purified material is shown in FIG. 3. Western blots under non-reducing conditions probed for kappa chain, E2 (linear epitope) or E2 (conformational epitope) all showed a band ~250 kDa, indicating assembled heavy and light chains with the gpE1 and gpE2 adducts. Moreover, the 250 kDa band is readily visible on a Coomassie stained gel, and indicates a high degree of purity. It was estimated that ~100 μg of purified fusion protein per gram of leaf tissue can be obtained with this system. Similar quantities of E2-H2 fusion protein alone can be also be obtained, which assembles disulfide-bonded dimers and is purified by protein A affinity. Guinea pigs can be immunized with E1-K3+E2-H2 complex or E2-H2 alone and assay anti-E2 antibody responses.

Insect cell expression of E2-661. A baculovirus recombinant clone was constructed with the soluble form of gpE2 (aa 384-661) fused to a 6-His tag, and using the baculovirus gp67 signal peptide for efficient secretion. Preliminary expression data indicate that E2-661 is secreted into the growth medium and can be purified by metal affinity. The insect cell E2-661 is used as a reference standard and capture antigen to assay anti-E2 antibody responses in animal immunization studies.

Figure 4:
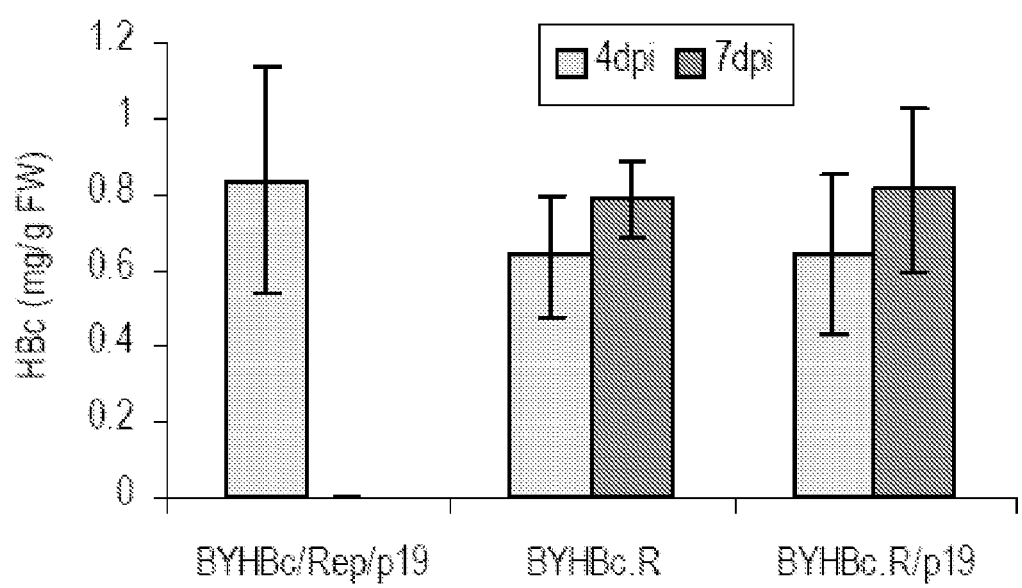

A DNA replicon system for rapid high-level production of vaccine antigens in plants. HCV polyprotein antigen expression in tobacco plants has encountered some difficulties in achieving high levels of antigen accumulation. To increase transient expression of vaccine antigens in plants, the inventors developed a geminiviral replicon vector system comprised of a bean yellow dwarf virus (BeYDV)-derived vector, a Rep/RepA-supplying vector and a P19 vector expressing the P19 protein of tomato bush stunt virus, a gene silencing inhibitor (see above). This system was validated using two antigens known to accumulate without phytoxicity in plants, thereby determining the overall efficacy of the new vector system. When hepatitis B core antigen (HBcAg) and Norwalk virus capsid protein (NVCP) were used as model antigens, they were produced at 0.80 and 0.34 mg/g leaf fresh weight. This three-component system was further simplified into a single replicon vector containing a built-in Rep/RepA cassette without affecting the yield of protein of interest (FIG. 4). The rapidity, simplicity, and high-yield potential of this vector system thus greatly enhance the commercial feasibility of vaccine production in plants.

Figure 5:
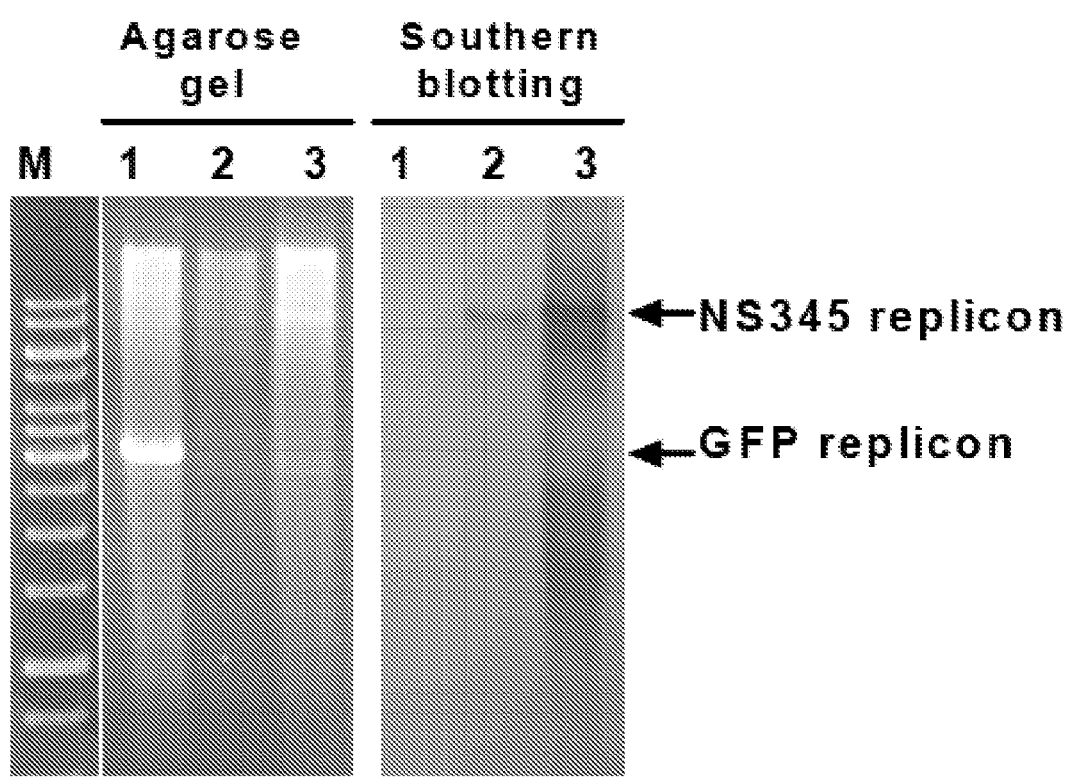
FIG. 5. Formation of DNA replicon in plant leaves infiltrated with pBY-NS345. Plant DNA was extracted from infiltrated leaves, digested with Xho I, run on agarose gel, blotted to membrane and detected with an NS3-specific probe. Lane M, 1 kb DNA ladder; lane 1, pBY-GFP infiltrated leaf sample; lane 2, leaf sample infiltrated with pBY-NS345 at OD600=0.025; lane 3, leaf sample infiltrated with pBY-NS345 at OD600=0.3.
Figure 6:
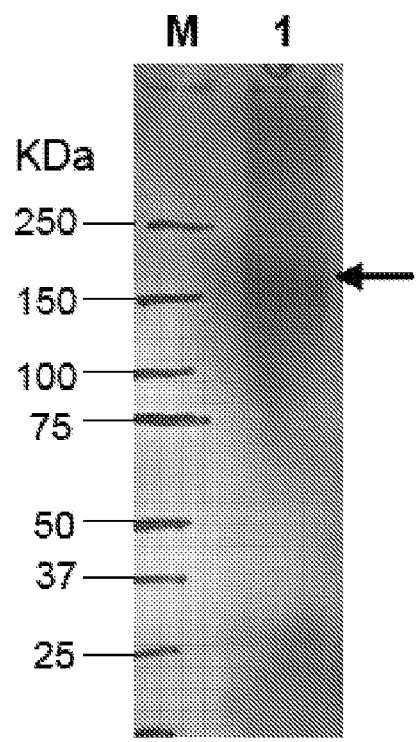
FIG. 6. Western blot analysis of polyprotein expression in pBY-NS345 infiltrated plant leaves. pBY-NS345 infiltrated leaves were homogenized in extraction buffer using a Fast-Prep machine. Leaf extract (lane 1) was then subjected to SDS-PAGE and Western blotting with an anti-NS3 antibody. The arrow indicates the presence of the fusion protein at an expected kD.

Transient expression of NS345 polyprotein using replicon vectors. After validating the vector system, the inventors constructed a replicon vector, pBY-NS345, in which the NS345 gene is under the control of cauliflower mosaic virus (CaMV) 35S promote for constitutive expression. Similarly replicon vectors, pBY-NS34, pBY-NS5C and pBY-NS5 were constructed for expressing NS34, NS5C and NS5 proteins, respectively. The vectors were introduced into *Agrobacterium* LBA4404. The resulting strains were used to infiltrate *Nicotiana benthamiana* (the host plant specie). Analysis of DNA extracted from infiltrated plant leaves by agarose gel electrophoresis and Southern blotting clearly showed the formation of ~8 kb NS345 replicon (FIG. 5). It was observed that the intensity of GFP replicon was much stronger than that of NS345 (FIG. 5). Considering the size of NS345, this result suggests formation of large replicons is less efficient than that of smaller replicons such as that for GFP. The NS345 protein accumulation was further evaluated with an anti-NS3 antibody (FIG. 6) on a Western blot. A ~170 KDa positive band was observed for leaf samples infiltrated with the NS345 replicon, but not with other vectors, suggesting the NS345 protein was correctly expressed.

Figure 7:
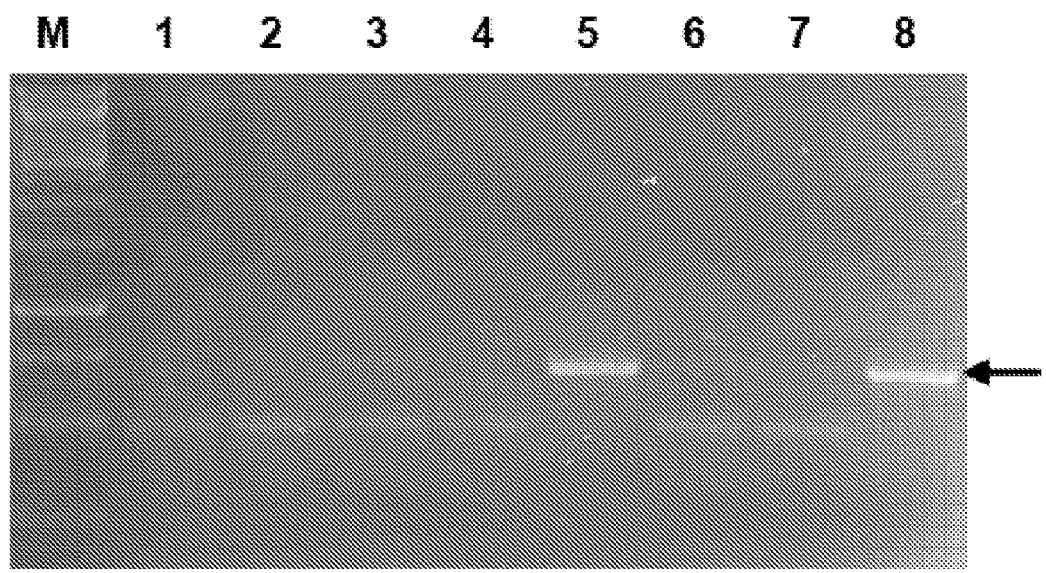
FIG. 7. Generation of pBY-NS345 transgenic plants. Binary vector pBY-NS345 was used to transform *N. benthamiana*. Plant DNA was extracted from regenerated Kanamycin-resistant plantlets (lanes 1-8) and used for PCR amplification with NS3-specific primers. The expected size of PCR products were ~0.7 KB as indicated by the arrow.
Figure 8:
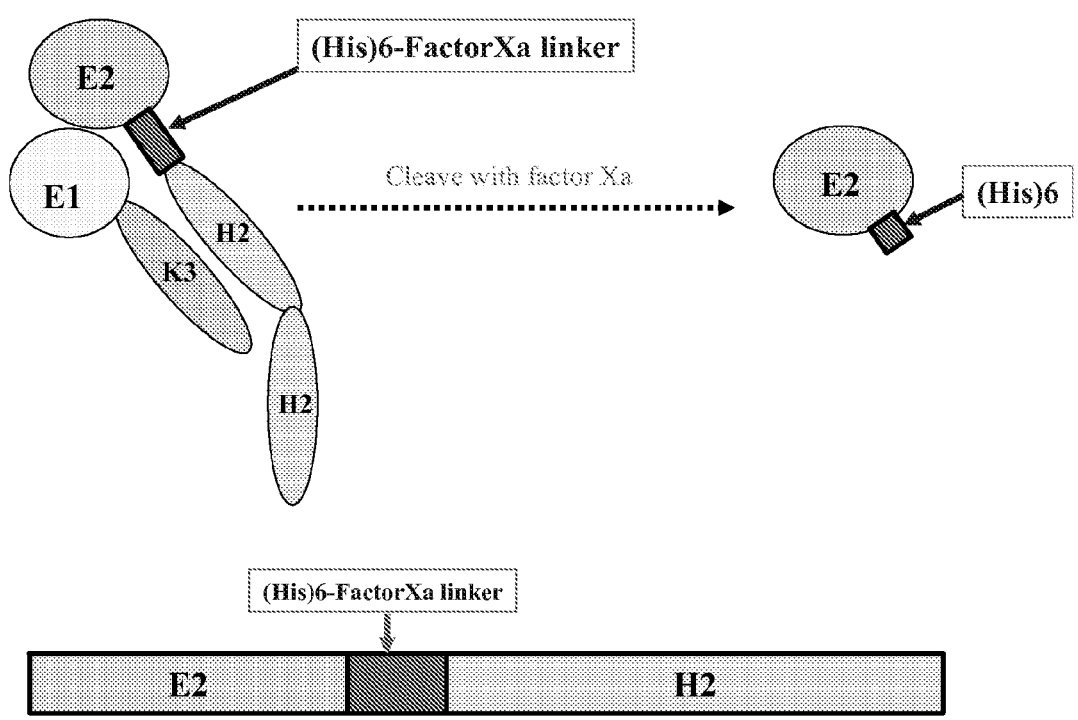
FIG. 8. Construction of E2(his6)XaH2 protein.

Generation of transgenic plants for stable expression of NS345 replicon. Gemini replicon vectors pBY-NS345 and pBY-NS34 were used to transform *N. benthamiana* to obtain stable transgenic plants. Kanamycin-resistant plantlets were screened by PCR with NS3-specific primers. Some positive lines were identified (FIG. 7).

EXAMPLE 3

Guinea Pig Immunization Study with HCV E1/E2-IgG Fusions

Immunogenicity of the IgG fusion antigens in Hartley guinea pigs was studied. The study groups were:

G1: immunized with 25 μg plant-derived gpE1/E2-IgG fusion proteins (E2-H2+E1-K3)

G2: immunized with 25 μg plant-derived gpE2-H chain fusion protein (E2-H2)

G3: immunized with 5 μg CHO cell-derived E1/E2 (obtained from Chiron/Novartis)

G4: animals placebo injected with PBS

Animals were immunized intramuscular on days 0, 28, and 56, using TiterMax adjuvant. They were sacrificed two weeks after the last dose, and serum obtained. The sera were assayed for reactivity with CHO cell derived His-tagged gpE2 (aa384-711) expressed using pcDNA™5/FRT (Invitrogen) and purified by metal affinity chromatography. Endpoint titers for total IgG were determined using 50 μg gpE2-711 per well, and are shown in Table 1. The data show that both plant-derived antigens elicited anti-E2 IgG levels comparable to the CHO cell derived antigen (Group 3, single animal). The difference in the mean titers of Groups 1 and 2 was not statistically significant. The guinea pig sera were sent to Nigel Bourne at UT-Galveston, Tex. for evaluation of HCV-neutralizing antibodies using a pseudovirus system. The data are shown in Table 1 (Neutr). One animal in each of the plant-derived antigen groups generated a level of HCV-neutralizing antibodies similar to the G3 animal that was immunized with CHO cell-derived antigen. The plant-derived gpE2 can evoke neutralizing antibodies in guinea pig. Further studies will examine effects of dose ranging and of other adjuvants including poly(I:C).

TABLE 1

Anti-gpE2 IgG and neutralizing (Neutr.) titers of guinea pigs immunized
with E2-H2/E1-K3 (G1), E2-H2 (G2), CHO cell gpE1/E2 (G3), or PBS (G4)

| G1   | IgG  | Neutr. | G2   | IgG  | Neutr. | G3   | IgG  | Neutr. | G4   | IgG  | Neutr. |
|------|------|--------|------|------|--------|------|------|--------|------|------|--------|
| G1.1 | 8000 | >1:80  | G2.1 | 1000 | >1:80  | G3.1 | 4000 | >1:80  | G4.1 | 200  | <1:10  |
| G1.2 | 500  | 1:10   | G2.2 | 4000 | 1:10   |      |      |        | G4.2 | 100  | 1:20   |
| G1.3 | 8000 | 1:10   | G2.3 | 1500 | <1:10  |      |      |        | G4.3 | 200  | <1:10  |
| G1.4 | 8000 | 1:10   | G2.4 | 500  | <1:10  |      |      |        |      |      |        |
| G1.5 | 500  | 1:20   | G2.5 | 2000 | 1:10   |      |      |        |      |      |        |
| G1.6 | 2000 | 1:20   | G2.6 | 8000 | 1:40   |      |      |        |      |      |        |
| G1.7 | 8000 | <1:10  | G2.7 | 8000 | <1:10  |      |      |        |      |      |        |
| Mean | 5000 |        |      | 3571 |        |      | 4000 |        |      | 167  |        |

EXAMPLE 4

Ebola Virus GP1 Fusion with MAB 6D8 Heavy Chain

This example describes expression of an immunoglobulin heavy chain fusion protein (GP1-H) that contains the Ebola virus glycoprotein (GP1) at its N-terminus. Previous studies (Phoolcharoen et al., 2011) showed the expression of an immunoglobulin heavy chain fusion protein (H-GP1) that contains the Ebola virus glycoprotein (GP1) at its C-terminus. The inventors reasoned that fusion of Ebola GP1 at the N-terminus instead may present the GP 1 in a more natural conformation, because in the viral envelope the GP1 N-terminus is free. Moreover, the inventors contemplate the co-expression of Ebola virus GP2 (a second envelope protein that associates with GP1), in a fusion protein (GP2-K) with an immunoglobulin light chain K3. Assembly of the GP1-H and GP2-K molecules to form an immunoglobulin (GP1-H::GP2-K)$_2$ may allow natural association of GP1 and GP2, which could generate a more potent vaccine antigen.

Construction of expression vector for GP1-H. The plant codon-optimized coding sequence for Ebola (Zaire) GP1 (GenBank Accession HM136775 (SEQ ID NO:32)) was amplified by PCR using the template pICgp1 (Mason et al., unpublished) and the primer IC-F (5'-CACCTCAC-CCATCTTTTATTAC (SEQ ID NO:33)) and the primer GP1dL-Bam-R (5'-cg ggatccacctccaccagatccaccTCCACCTGTGATCAGGCC (SEQ ID NO:34)), which adds a segment encoding the linker "GGSGGGS" (SEQ ID NO:35) and a BamHI site to the 3' end of the GP1 cds at amino acid Gly-464. The PCR reaction used a high-fidelity thermostable DNA polymerase (Phusion®, on the world wide web at neb.com/nebecomm/products/productF-553.asp). The amplicon contains the coding sequence for a signal peptide (MGWSCIILFLVATATGVHS (SEQ ID NO:36)), which will direct the protein co-translationally to the endoplasmic reticulum (ER) in eukaryotic cells. The 1547 bp PCR product was digested with NcoI-BamHI and inserted into the vector pICgp1/NcoI-BamHI, to replace its existing NcoI-BamHI fragment and produce pICgp1d. DNA sequencing confirmed the modified GP1 sequence, which was then obtained by digestion of pICgp1d with NcoI-BamHI, and ligated with the vector pBYRm2 digested AscI-KpnI, and DNA fragments pBY034 (Mor et al., 2003) digested AscI-NcoI, and pBYR-E2H2 digested BamHI-KpnI. The latter BamHI-KpnI fragment provides the coding sequence for the mAb 6D8 heavy chain, which is fused to the GP1-linker DNA by the BamHI site. The GP1-H expression vector is called pBYR-gp1dH2.

Expression of GP1-H2 fusion protein. pBYR-gp1dH2 was mobilized into *Agrobacterium tumefaciens* GV3101 by electroporation, and selected clones were grown in liquid culture to prepare glycerol stocks for storage at −80° C. Plasmids prepared from the *Agrobacterium* clones were verified by restriction digestion to validate the bacterial lines. *Nicotiana benthamiana* plants (~5 weeks old) were inoculated by blunt syringe infiltration into mature leaves with *Agrobacterium* cultures at a density that yielded O.D. at 600 nm=0.2. Bacterial line GV3101/pBYR-gp1H2 was delivered either with or without GV3101/pBYK3R, which contains an expression cassette for the mAb 6D8 light chain K3. After 3 days, the inoculation sites appeared healthy, suggesting that the usual toxic effects of GP1 expression (Phoolcharoen et al., 2011) were mitigated by fusion with the IgG H chain.

Figure 9:
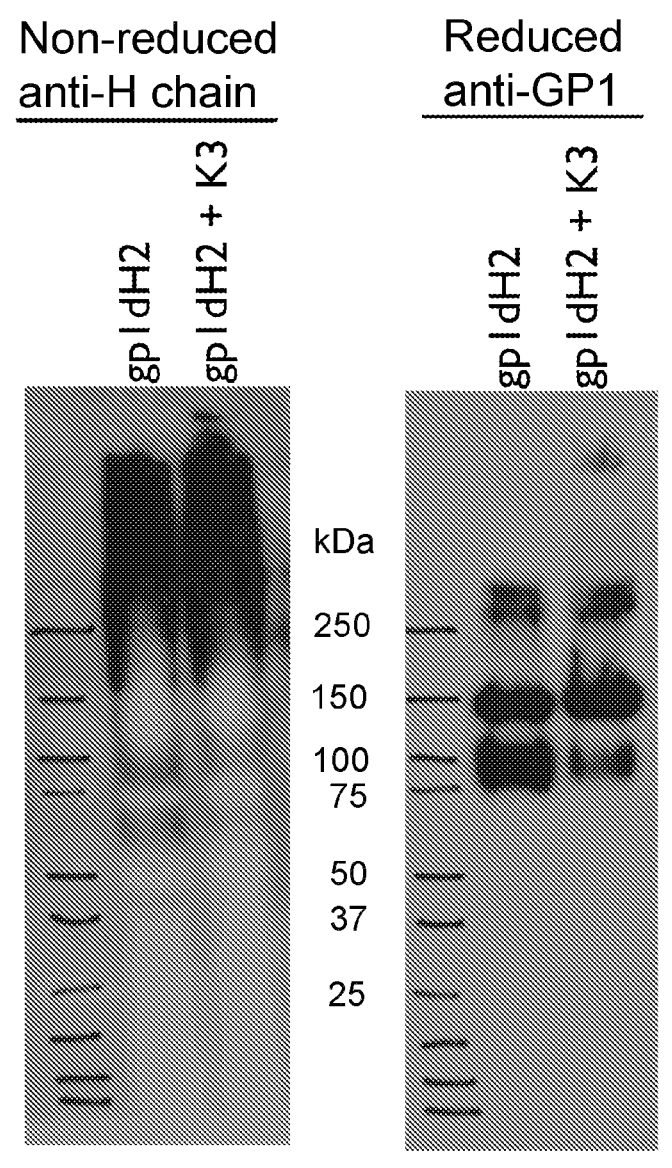

The 3-day leaf samples were obtained and extracted in SDS sample buffer without reducing agent. Aliquots were electrophoresed in 4-15% acrylamide gradient gels (Bio-Rad), either without reducing agent and without heating, or after reducing treatment by addition of 200 mM diothiothreitol (DTT) and heating at 100° C. for 5 min. The gels were electro-blotted to PVDF membranes and probed with goat anti-human IgG (gamma chain)-HRP (for non-reducing gel), or mouse mAb 6D8 anti-Ebola GP1 followed by goat anti-mouse IgG-HRP. The results in FIG. 9 show that most signal from the anti-H chain probe occurred at high molecular weight, indicating assembly of the GP1-H dimer into an immunoglobulin-like structure. Co-expression of the light chain (K3) with GP1-H may have increased the signal somewhat. Very faint signals at ~100 kDa and ~65 kDa indicate that proteolytic degradation of the fusion protein was minimal. The same samples under reducing conditions and probed with anti-GP1 mAb 6D8 showed strong bands at ~100 kDa and ~140 kDa. The difference in the sizes may be due to differences in glycosylation states of the GP1 protein. When the K3 light chain was co-expressed, a substantially greater proportion of the protein occurred in the 140 kDa species.

Thus, Ebola virus GP1 can be readily expressed as a fusion protein at the N-terminus of a human IgG heavy chain, and assembles Ig-like structures.

EXAMPLE 5

Co-Expression of E2H and E2K

Figure 10:
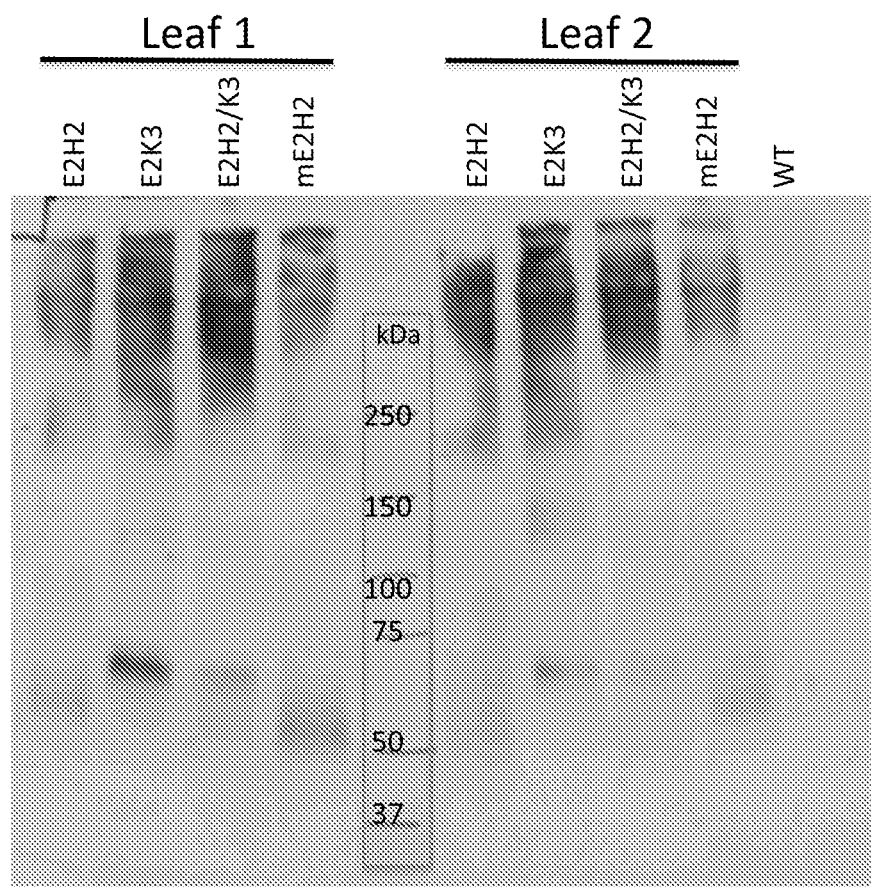

The inventors co-expressed gpE2 fusions with heavy chain (gamma) and light chain (kappa) in order to allow immunoglobulin assembly to form (E2H::E2K)$_2$. They reasoned that gpE2 might form a dimer that reflects the natural structure of gpE2 in the viral envelope. The plasmids pBYR-E2H2 and pBYR-E2K3 were described in Example 2 and FIG. 2. pBYRmE2H2 was constructed by substitution of a coding sequence for the mouse IgG2a heavy chain from mAb 278.02 (Chargelegue et al., 2005) for the human gamma chain sequence in pBYR-E2H2. *Agrobacterium* lines harboring pBYR-E2H2 or pBYR-E2K3 were infiltrated into leaves of *N. benthamiana* either alone or together, and pBYRmE2H2 was delivered alone. Leaf samples were collected 3 days after agro-inoculation, extracted with SDS sample buffer lacking reducing agent, and proteins resolved by electrophoresis in a 4-15% acrylamide gradient gel. The proteins were transferred to a PVDF membrane and probed with guinea pig anti-gpE1/E2 serum (from a guinea pig immunized with gpE1/E2 expressed in Chinese hamster ovary cells). The Western blot in FIG. 10 shows that E2 protein is found in high molecular weight protein species, indicating the presence of full-length fusion proteins. Moreover, co-expression of E2H2 and E2K3 resulted in higher levels of high molecular weight E2 protein, suggesting that co-expression allowed assembly of immunoglobulin-like complexes and stabilized the gpE2 protein.

REFERENCES

The following references, to the extent that they provide exemplary procedural or other details supplementary to those set forth herein, are specifically incorporated herein by reference.

U.S. Pat. Nos. 3,791,932
3,949,064
4,174,384
4,554,101
4,578,770
4,596,792
4,599,230
4,599,231
4,601,903
4,608,251
4,683,202
4,684,611
4,879,236
4,952,500
5,084,269
5,302,523
5,322,783
5,384,253
5,464,765
5,538,877
5,538,880
5,550,318
5,563,055
5,580,859
5,589,466
5,591,616
5,610,042
5,656,610
5,702,932
5,736,524
5,780,448
5,789,215
5,871,986
5,925,565
5,928,906
5,935,819
5,945,100
5,981,274
5,994,624
6,651,655
6,656,462
6,733,754
6,793,923
6,814,971

Alter et al., *N. Engl. J. Med.*, 341:556-562, 1999.
Ausubel et al., In: *Current Protocols in Molecular Biology*, John, Wiley & Sons, Inc, NY, 1994; 1996.
Canizares et al., *Immunol. Cell Biol.*, 83(3):263-70, 2005.
Chargelegue et al., *Infect. Immun.* 73, 5915-5922, 2005.
Chen, *Biological Engineering*, 1(4):291-321, 2008.
Chen and Okayama, *Mol. Cell Biol.*, 7(8):2745-2752, 1987.
Delwaide et al. *Rev. Med. Liege*, 55:337-340, 2000.
Dietrich and Maiss, *J. Gen. Virol.*, 84(Pt 10):2871-6, 2003.
Diveki et al., *Biochimie.*, 84(10):997-1002, 2002.
Fechheimer et al., *Proc Natl. Acad. Sci. USA*, 84:8463-8467, 1987.
Fiedler et al., *Bio/Technology*, 13:1090-1093, 1995.
Floss et al., *Transgenic Res.*, 16(3):315-332, 2007.
Fraley et al., *Proc. Natl. Acad. Sci. USA*, 76:3348-3352, 1979.
Friedrichsen et al., *Plant Physiol.*, 123(4):1247-56, 2000.
Giddings, *Curr. Opin. Biotechnol.*, 12(5):450-4, 2001.
Giddings et al., *Nat. Biotechnol.*, 18(11):1151-1155, 2000.
Giritch et al., *Proc. Natl. Acad. Sci. USA*, 103(40):14701-6, 2006.
Gleba et al., *Curr. Opin. Biotechnol.*, 18(2):134-41, 2007.
Gopal, *Mol. Cell Biol.*, 5:1188-1190, 1985.
Graham and Van Der Eb, *Virology*, 52:456-467, 1973.
Harland and Weintraub, *J. Cell Biol.*, 101(3):1094-1099, 1985.
Harlow and Lane, In: *Antibodies: A Laboratory Manual*, Cold Spring Harbor Laboratory, Cold Spring Harbor, N.Y., 346-348, 1988.
Hendy et al., *J. Immunol. Methods*, 231:137-146, 1999.
Hiatt et al., *Nature*, 342(6245):76-8, 1989.
Hood et al., *Curr. Opin. Biotechnol.*, 13(6):630-5, 2002.
Hoofnagle, *Hepatology*, 36:S21-S29, 2002.
Huang et al., *Biotechnol. Bioeng.*, 103:706-714, 2009.
Huang and Mason, *Plant Biotechnol. J.*, 2:241-249, 2004.
Huang et al., *Biotechnol. Bioeng.*106: 9-17, 2010.
Hull and Plaskitt, *Virology*, 42(3):773-6, 1970.
Inouye and Inouye, *Nucleic Acids Res.*, 13:3101-3109, 1985.
Judge et al., *Infect. Immun.*, 72(1):168-75, 2004.
Kaeppler et al., *Plant Cell Rep.*, 8:415-418, 1990.
Kaneda et al., *Science*, 243:375-378, 1989.
Kato et al, *J. Biol. Chem.*, 266:3361-3364, 1991.
Kyte and Doolittle, *J. Mol. Biol.*, 157(1):105-132, 1982.
Larrick et al., *Res. Immunol.*, 149:603-608, 1998.
Lico et al., *J. Cell Physiol.*, 216(2):366-77, 2008.
Lindenbach and Rice, *Nature*, 436:933-938, 2005.
Lohmann et al., *J. Hepatol.*, 24:11-19, 1996.
Ma et al., *Nature, (Genetics)*, 4:794-805, 2003.
Ma et al., *Vaccine*, 23(15):1814-8, 2005.
Macejak and Sarnow, *Nature*, 353:90-94, 1991.
Marillonnet et al., *Proc. Natl. Acad. Sci. USA*, 101(18): 6852-7, 2004.
Mor et al., *Biotechnol. Bioeng.*, 81(4):430-37, 2003.
Nicolau and Sene, *Biochim. Biophys. Acta*, 721:185-190, 1982.
Nicolau et al., *Methods Enzymol.*, 149:157-176, 1987.
Omirulleh et al., *Plant Mol. Biol.*, 21(3):415-428, 1993.
PCT Appln. WO 94/09699
PCT Appln. W095/06128
Pelletier and Sonenberg, *Nature*, 334(6180):320-325, 1988.
Penin et al., *J. Hepatol.*, 24:11-19, 2004.
Phoolcharoen et al., *Plant Biotechnol J.* in press 2011.

Potrykus et al., *Mol. Gen. Genet.*, 199(2):169-177, 1985.
Potrykus et al., *Mol. Gen. Genet.*, 199:183-188, 1985.
Remington's Pharmaceutical Sciences" 15th Ed., 1035-1038 and 1570-1580, 1990.
Rippe, et al., *Mol. Cell Biol.*, 10:689-695, 1990.
Sambrook and Russell, Molecular Cloning: A Laboratory Manual 3rd Ed., Cold Spring Harbor Laboratory Press, 2001.
Santi et al., *Methods*, 40(1):66-76, 2006.
Santi et al., *Vaccine*, 26(15):1846-1854, 2008.
Stoger et al., *Methods Mol. Biol.*, 248:301-18, 2004.
Tacket et al., *J. Infect. Dis.*, 2000 July; 182(1):302-5, 2000.
Thanavala et al., *Proc. Natl. Acad. Sci. USA*, 102(9):3378-82, 2005.
Thanavala et al., *Expert Rev. Vaccines*, 5(2):249-60, 2006.
Twyman et al., *Expert Opin. Emerg. Drugs*, 10(1):185-218, 2005.
Vitale and Pedrazzini, *Mol. Interv.*, 5(4):216-25, 2005.
Wilson et al., *Science*, 287(5458):1664-6, 2000.
Wong et al., *Gene*, 10:87-94, 1980.
Yusibov et al., *Drugs*, 7(4):203-17, 2006.

What is claimed is:

1. A polypeptide composition comprising:
   a first polypeptide consisting essentially of an amino acid sequence that is at least 98% identical to SEQ ID NO:9 or SEQ ID NO:11; and
   a second polypeptide comprising a carboxy terminal light chain immunoglobulin polypeptide and an amino terminal glycoprotein polypeptide,
   wherein the first and second polypeptides are in a complex forming at least one heterodimeric polypeptide.

2. The composition of claim 1, wherein the glycoprotein of the second polypeptide is a Hepatitis C virus glycoprotein.

3. The composition of claim 2 wherein the glycoprotein of the second polypeptide is an HCV E2 or E1 glycoprotein, wherein the first polypeptide and the viral glycoprotein of the second polypeptide assemble to form an HCVE1/E2 glycoprotein complex.

4. The composition of claim 3, wherein the HCV E1 glycoprotein segment of the second polypeptide consists essentially of an amino acid sequence that is at least 90% identical to SEQ ID NO:4.

5. The composition of claim 1, wherein the second polypeptide consists essentially of an amino acid sequence that is at least 90% identical to SEQ ID NO:10 or SEQ ID NO:12.

6. A polypeptide composition comprising:
   a first polypeptide comprising a carboxy terminal immunoglobulin heavy chain polypeptide and an amino terminal glycoprotein polypeptide; and
   a second polypeptide consisting essentially of an amino acid sequence that is at least 99% identical to SEQ ID NO:10 or SEQ ID NO:12,
   wherein the first and second polypeptides are in a complex forming at least one heterodimeric polypeptide.

7. The composition of claim 1, further comprising a polypeptide tetramer comprising two first polypeptides and two second polypeptides.

8. The composition of claim 1, wherein the first polypeptide and/or the second polypeptide further comprise one or more of a histidine tag and/or a protease cleavage site.

9. A pharmaceutical and/or vaccine composition capable of treating and/or preventing a viral infection, the pharmaceutical and/or vaccine composition comprising the composition of claim 1 and a pharmaceutically acceptable excipient, wherein the pharmaceutical and/or vaccine composition is capable of eliciting an immune response to the first and/or second polypeptide.

10. The composition of claim 6, wherein the glycoprotein of the first polypeptide is a Hepatitis C virus glycoprotein.

11. The composition of claim 10, wherein the glycoprotein of the first polypeptide is an HCV E2 or E1 glycoprotein, wherein the second polypeptide and the viral glycoprotein of the first polypeptide assemble to form an HCVE1/E2 glycoprotein complex.

12. The composition of claim 11, wherein the HCV E1 glycoprotein segment of the first polypeptide consists essentially of an amino acid sequence that is at least 90% identical to SEQ ID NO:4.

13. The composition of claim 6, wherein the first polypeptide consists essentially of an amino acid sequence that is at least 80% identical to SEQ ID NO:9 or SEQ ID NO:11.

14. The composition of claim 6, further comprising a polypeptide tetramer comprising two first polypeptides and two second polypeptides.

15. The composition of claim 6, wherein the first polypeptide and/or the second polypeptide further comprise one or more of a histidine tag and/or a protease cleavage site.

16. A pharmaceutical and/or vaccine composition capable of treating and/or preventing a viral infection, the pharmaceutical and/or vaccine composition comprising the composition of claim 6 and a pharmaceutically acceptable excipient, wherein the pharmaceutical and/or vaccine composition is capable of eliciting an immune response to the first and/or second polypeptide.

\* \* \* \* \*